United States Patent
Burke et al.

(10) Patent No.: US 8,142,721 B2
(45) Date of Patent: *Mar. 27, 2012

(54) TEST STRIP WITH SLOT VENT OPENING

(75) Inventors: David W. Burke, Carmel, IN (US); Michael Marquant, Mannheim (DE)

(73) Assignees: Roche Diagnostics Operations, Inc., Indianapolis, IN (US); Roche Operations Ltd., Hamilton (BM)

( * ) Notice: Subject to any disclaimer, the term of this patent is extended or adjusted under 35 U.S.C. 154(b) by 0 days.

This patent is subject to a terminal disclaimer.

(21) Appl. No.: 12/888,990

(22) Filed: Sep. 23, 2010

(65) Prior Publication Data
US 2011/0011738 A1     Jan. 20, 2011

Related U.S. Application Data

(62) Division of application No. 10/871,468, filed on Jun. 18, 2004, now Pat. No. 7,829,023.

(60) Provisional application No. 60/480,397, filed on Jun. 20, 2003.

(51) Int. Cl.
G01N 33/48 (2006.01)

(52) U.S. Cl. ............ 422/82.01; 422/401; 422/412; 204/403.01

(58) Field of Classification Search ........... 422/82.01, 422/401, 412; 72/403.01
See application file for complete search history.

(56) References Cited

U.S. PATENT DOCUMENTS

| | | | |
|---|---|---|---|
| 3,715,192 A | 2/1973 | Wenz et al. | |
| 3,980,437 A | 9/1976 | Kishimoto et al. | |
| 4,065,263 A | 12/1977 | Woodbridge, III | |
| 4,225,410 A | 9/1980 | Pace | |
| 4,420,564 A | 12/1983 | Tsuji et al. | |
| 4,476,149 A | 10/1984 | Poppe et al. | |
| 4,510,383 A | 4/1985 | Ruppender | |

(Continued)

FOREIGN PATENT DOCUMENTS
CN    1 467 496 A    5/2003
(Continued)

OTHER PUBLICATIONS

Aoki, Koichi et al.; Theory of Chronoamperometric Curves at Microband Electrodes; J. Electroanal. Chem.; 1987; 19-32; 225; The Netherlands.
(Continued)

*Primary Examiner* — Lyle Alexander
(74) *Attorney, Agent, or Firm* — Woodard, Emhardt, Moriarty, McNett & Henry LLP

(57) ABSTRACT

A test strip with a covering layer having a novel slot. The slot divides the inventive covering layer into two parts and provides a vent opening that allows air to escape as fluid enters a cavity or sample receiving chamber formed in the test strip. In preferred embodiments, the covering layer is clear such that the user can see through it and the slot doubles as a "fill line." The user can thus watch the fluid sample enter the test strip, progress through the capillary cavity, and then stop at the slot or fill-line. This provides positive assurance to the user that the sample size is sufficient and the test strip has been filled properly. The present invention also provides an advantageous method of mass-producing the inventive test strips without having to align the slot or vent opening laterally with respect to the test strips and without having to punch a vent opening. The method is also well suited to mass production by roll processing techniques.

23 Claims, 13 Drawing Sheets

U.S. PATENT DOCUMENTS

| | | |
|---|---|---|
| 4,545,382 A | 10/1985 | Higgins et al. |
| 4,571,292 A | 2/1986 | Liu et al. |
| 4,578,716 A | 3/1986 | Van Rijckevorsel et al. |
| 4,592,893 A | 6/1986 | Poppe et al. |
| 4,671,288 A | 6/1987 | Gough |
| 4,679,562 A | 7/1987 | Luksha |
| 4,713,165 A | 12/1987 | Conover et al. |
| 4,714,874 A | 12/1987 | Morris et al. |
| 4,789,804 A | 12/1988 | Karube et al. |
| 4,797,256 A | 1/1989 | Watlington, IV |
| 4,805,624 A | 2/1989 | Yao et al. |
| 4,877,580 A | 10/1989 | Aronowitz et al. |
| 4,897,173 A | 1/1990 | Nankai et al. |
| 4,927,516 A | 5/1990 | Yamaguchi et al. |
| 4,935,105 A | 6/1990 | Churchouse |
| 4,938,860 A | 7/1990 | Wogoman |
| 4,970,145 A | 11/1990 | Bennetto et al. |
| 5,049,487 A | 9/1991 | Phillips et al. |
| 5,059,394 A | 10/1991 | Phillips et al. |
| 5,066,372 A | 11/1991 | Wetall |
| 5,120,420 A | 6/1992 | Nankai et al. |
| 5,122,244 A | 6/1992 | Hoenes et al. |
| 5,141,850 A | 8/1992 | Cole et al. |
| 5,141,868 A | 8/1992 | Shanks et al. |
| 5,143,694 A | 9/1992 | Schafer et al. |
| 5,179,005 A | 1/1993 | Phillips et al. |
| 5,187,100 A | 2/1993 | Matzinger et al. |
| 5,192,415 A | 3/1993 | Yoshioka et al. |
| 5,243,516 A | 9/1993 | White |
| 5,250,439 A | 10/1993 | Musho et al. |
| 5,264,103 A | 11/1993 | Yoshioka et al. |
| 5,266,179 A | 11/1993 | Nankai et al. |
| 5,281,395 A | 1/1994 | Markart et al. |
| 5,286,362 A | 2/1994 | Hoenes et al. |
| 5,288,636 A | 2/1994 | Pollmann et al. |
| 5,296,192 A | 3/1994 | Carroll et al. |
| 5,304,468 A | 4/1994 | Phillips et al. |
| 5,306,623 A | 4/1994 | Kiser et al. |
| 5,312,762 A | 5/1994 | Guiseppi-Elie |
| 5,344,754 A | 9/1994 | Zweig |
| 5,366,609 A | 11/1994 | White et al. |
| 5,379,214 A | 1/1995 | Arbuckle et al. |
| 5,385,846 A | 1/1995 | Kuhn et al. |
| 5,389,215 A | 2/1995 | Horiuchi et al. |
| 5,395,504 A | 3/1995 | Saurer et al. |
| 5,413,690 A | 5/1995 | Kost et al. |
| 5,413,764 A | 5/1995 | Haar |
| 5,418,142 A | 5/1995 | Kiser et al. |
| 5,421,189 A | 6/1995 | Dussault |
| 5,424,035 A | 6/1995 | Hones et al. |
| 5,426,032 A | 6/1995 | Phillips et al. |
| 5,437,999 A | 8/1995 | Diebold et al. |
| 5,438,271 A | 8/1995 | White et al. |
| 5,439,826 A | 8/1995 | Kontorovich |
| 5,469,846 A | 11/1995 | Khan |
| 5,470,533 A | 11/1995 | Shindo et al. |
| 5,494,638 A | 2/1996 | Gullick |
| 5,508,171 A | 4/1996 | Walling et al. |
| 5,509,410 A | 4/1996 | Hill et al. |
| 5,515,170 A | 5/1996 | Matzinger et al. |
| 5,526,120 A | 6/1996 | Jina et al. |
| 5,547,702 A | 8/1996 | Gleisner |
| 5,552,116 A | 9/1996 | Yokota et al. |
| 5,554,531 A | 9/1996 | Zweig |
| 5,563,042 A | 10/1996 | Phillips et al. |
| 5,569,608 A | 10/1996 | Sommer |
| 5,575,895 A | 11/1996 | Ikeda et al. |
| 5,575,930 A | 11/1996 | Tietje-Girault et al. |
| 5,580,794 A | 12/1996 | Allen |
| 5,582,697 A | 12/1996 | Ikeda et al. |
| 5,597,532 A | 1/1997 | Connolly |
| 5,605,837 A | 2/1997 | Karimi et al. |
| 5,620,579 A | 4/1997 | Genshaw et al. |
| 5,620,863 A | 4/1997 | Tomasco et al. |
| 5,627,075 A | 5/1997 | Bateson |
| 5,628,890 A | 5/1997 | Carter et al. |
| 5,645,798 A | 7/1997 | Schreiber et al. |
| 5,650,062 A | 7/1997 | Ikeda et al. |
| 5,653,863 A | 8/1997 | Genshaw et al. |
| 5,656,502 A | 8/1997 | MacKay et al. |
| 5,658,443 A | 8/1997 | Yamamoto et al. |
| 5,665,215 A | 9/1997 | Bussmann et al. |
| 5,670,031 A | 9/1997 | Hintsche et al. |
| 5,682,884 A | 11/1997 | Hill et al. |
| 5,691,486 A | 11/1997 | Behringer et al. |
| 5,695,623 A | 12/1997 | Michel et al. |
| 5,708,247 A | 1/1998 | McAleer et al. |
| 5,720,862 A | 2/1998 | Hamamoto et al. |
| 5,723,284 A | 3/1998 | Ye |
| 5,727,548 A | 3/1998 | Hill et al. |
| 5,757,666 A | 5/1998 | Schreiber et al. |
| 5,762,770 A | 6/1998 | Pritchard et al. |
| 5,780,304 A | 7/1998 | Matzinger et al. |
| 5,788,833 A | 8/1998 | Lewis et al. |
| 5,789,255 A | 8/1998 | Yu |
| 5,798,031 A | 8/1998 | Charlton et al. |
| 5,843,691 A | 12/1998 | Douglas et al. |
| 5,846,744 A | 12/1998 | Athey et al. |
| 5,849,174 A | 12/1998 | Sanghera et al. |
| 5,856,195 A | 1/1999 | Charlton et al. |
| 5,869,972 A | 2/1999 | Birch et al. |
| 5,890,489 A | 4/1999 | Elden |
| 5,904,898 A | 5/1999 | Markart |
| 5,911,872 A | 6/1999 | Lewis et al. |
| 5,916,156 A | 6/1999 | Hildenbrand et al. |
| 5,921,925 A | 7/1999 | Cartmell et al. |
| 5,945,341 A | 8/1999 | Howard, III |
| 5,951,836 A | 9/1999 | McAleer et al. |
| 5,965,380 A | 10/1999 | Heller et al. |
| 5,968,760 A | 10/1999 | Phillips et al. |
| 5,989,917 A | 11/1999 | McAleer et al. |
| 5,997,817 A | 12/1999 | Crismore et al. |
| 6,004,441 A | 12/1999 | Fujiwara et al. |
| 6,036,919 A | 3/2000 | Thym et al. |
| 6,044,285 A | 3/2000 | Chaiken et al. |
| 6,071,391 A | 6/2000 | Gotoh et al. |
| 6,087,182 A | 7/2000 | Jeng et al. |
| 6,091,975 A | 7/2000 | Daddona et al. |
| 6,102,872 A | 8/2000 | Doneen et al. |
| 6,103,033 A | 8/2000 | Say et al. |
| 6,120,676 A | 9/2000 | Heller et al. |
| 6,121,009 A | 9/2000 | Heller et al. |
| 6,121,050 A | 9/2000 | Han |
| 6,129,823 A | 10/2000 | Hughes et al. |
| 6,134,461 A | 10/2000 | Say et al. |
| 6,143,164 A | 11/2000 | Heller et al. |
| 6,144,869 A | 11/2000 | Berner et al. |
| 6,150,124 A | 11/2000 | Riedel |
| 6,153,069 A | 11/2000 | Pottgen et al. |
| 6,156,173 A | 12/2000 | Gotah et al. |
| 6,159,745 A | 12/2000 | Roberts et al. |
| 6,162,611 A | 12/2000 | Heller et al. |
| 6,162,639 A | 12/2000 | Douglas |
| 6,168,957 B1 | 1/2001 | Matzinger et al. |
| 6,170,318 B1 | 1/2001 | Lewis |
| 6,174,420 B1 | 1/2001 | Hodges et al. |
| 6,175,752 B1 | 1/2001 | Say et al. |
| 6,176,988 B1 | 1/2001 | Kessler |
| 6,179,979 B1 | 1/2001 | Hodges et al. |
| 6,180,062 B1 | 1/2001 | Naka et al. |
| 6,193,873 B1 | 2/2001 | Ohara et al. |
| 6,200,773 B1 | 3/2001 | Ouyang et al. |
| 6,225,078 B1 | 5/2001 | Ikeda et al. |
| 6,241,862 B1 | 6/2001 | McAleer et al. |
| 6,251,260 B1 | 6/2001 | Heller et al. |
| 6,258,229 B1 | 7/2001 | Winarta et al. |
| 6,258,254 B1 | 7/2001 | Miyamoto et al. |
| 6,259,937 B1 | 7/2001 | Schulman et al. |
| 6,268,162 B1 | 7/2001 | Phillips et al. |
| 6,270,637 B1 | 8/2001 | Crismore et al. |
| 6,271,044 B1 | 8/2001 | Ballerstadt et al. |
| 6,277,641 B1 | 8/2001 | Yager |
| 6,281,006 B1 | 8/2001 | Heller et al. |
| 6,284,125 B1 | 9/2001 | Hodges et al. |
| 6,284,550 B1 | 9/2001 | Carroll et al. |
| 6,287,451 B1 | 9/2001 | Winarta et al. |
| 6,287,595 B1 | 9/2001 | Loewy et al. |

| Patent Number | Date | Inventor |
|---|---|---|
| 6,295,506 B1 | 9/2001 | Heinonen et al. |
| 6,299,757 B1 | 10/2001 | Feldman et al. |
| 6,300,123 B1 | 10/2001 | Vadgama et al. |
| 6,300,141 B1 | 10/2001 | Segal et al. |
| 6,300,142 B1 | 10/2001 | Andrewes et al. |
| 6,309,526 B1 | 10/2001 | Fujiwara et al. |
| 6,315,951 B1 | 11/2001 | Markart |
| 6,316,264 B1 | 11/2001 | Corey et al. |
| 6,325,917 B1 | 12/2001 | Maxwell et al. |
| 6,329,161 B1 | 12/2001 | Heller et al. |
| 6,331,438 B1 | 12/2001 | Aylott et al. |
| 6,335,203 B1 | 1/2002 | Patel et al. |
| 6,338,790 B1 | 1/2002 | Feldman et al. |
| 6,340,428 B1 | 1/2002 | Ikeda et al. |
| 6,349,230 B1 | 2/2002 | Kawanaka |
| 6,377,894 B1 | 4/2002 | Deweese et al. |
| 6,377,896 B1 | 4/2002 | Sato et al. |
| 6,379,513 B1 | 4/2002 | Chambers et al. |
| 6,395,227 B1 | 5/2002 | Kiser et al. |
| 6,413,395 B1 | 7/2002 | Bhullar et al. |
| 6,413,410 B1 | 7/2002 | Hodges et al. |
| 6,420,128 B1 | 7/2002 | Ouyang et al. |
| 6,444,115 B1 | 9/2002 | Hodges et al. |
| 6,447,657 B1 | 9/2002 | Bhullar et al. |
| 6,454,921 B1 | 9/2002 | Hodges et al. |
| 6,458,258 B2 | 10/2002 | Taniike et al. |
| 6,461,496 B1 | 10/2002 | Feldman et al. |
| 6,475,360 B1 | 11/2002 | Hodges et al. |
| 6,475,372 B1 | 11/2002 | Ohara et al. |
| 6,484,046 B1 | 11/2002 | Say et al. |
| 6,485,923 B1 | 11/2002 | Yani et al. |
| 6,488,827 B1 | 12/2002 | Shartle |
| 6,489,133 B2 | 12/2002 | Phillips et al. |
| 6,491,803 B1 | 12/2002 | Shen et al. |
| 6,491,870 B2 | 12/2002 | Patel et al. |
| 6,501,976 B1 | 12/2002 | Sohrab |
| 6,503,381 B1 | 1/2003 | Gotoh et al. |
| 6,514,718 B2 | 2/2003 | Heller et al. |
| 6,514,769 B2 | 2/2003 | Lee |
| 6,521,110 B1 | 2/2003 | Hodges et al. |
| 6,521,182 B1 | 2/2003 | Shartle et al. |
| 6,525,330 B2 | 2/2003 | Paolini et al. |
| 6,525,549 B1 | 2/2003 | Poellmann |
| 6,526,298 B1 | 2/2003 | Khalil et al. |
| 6,531,040 B2 | 3/2003 | Musho et al. |
| 6,531,322 B1 | 3/2003 | Jurik et al. |
| 6,540,890 B1 | 4/2003 | Bhullar et al. |
| 6,540,891 B1 | 4/2003 | Stewart et al. |
| 6,541,266 B2 | 4/2003 | Modzelewski et al. |
| 6,544,474 B2 | 4/2003 | Douglas |
| 6,549,796 B2 | 4/2003 | Sohrab |
| 6,551,494 B1 | 4/2003 | Heller et al. |
| 6,555,061 B1 | 4/2003 | Leong et al. |
| 6,558,528 B1 | 5/2003 | Matzinger |
| 6,560,471 B1 | 5/2003 | Heller et al. |
| 6,561,978 B1 | 5/2003 | Conn et al. |
| 6,561,989 B2 | 5/2003 | Whitson |
| 6,565,509 B1 | 5/2003 | Plante et al. |
| 6,565,738 B1 | 5/2003 | Henning et al. |
| 6,571,651 B1 | 6/2003 | Hodges |
| 6,572,822 B2 | 6/2003 | Jurik et al. |
| 6,576,101 B1 | 6/2003 | Heller et al. |
| 6,576,117 B1 | 6/2003 | Iketaki et al. |
| 6,576,416 B2 | 6/2003 | Haviland et al. |
| 6,576,461 B2 | 6/2003 | Heller et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,594,514 B2 | 7/2003 | Berner et al. |
| 6,599,406 B1 | 7/2003 | Kawanaka et al. |
| 6,599,407 B2 | 7/2003 | Taniike et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,603 B2 | 9/2003 | Yaralli et al. |
| 6,618,934 B1 | 9/2003 | Feldman et al. |
| 6,627,057 B1 | 9/2003 | Bhullar et al. |
| 6,632,349 B1 | 10/2003 | Hodges et al. |
| 6,638,415 B1 | 10/2003 | Hodges et al. |
| 6,638,716 B2 | 10/2003 | Heller et al. |
| 6,645,359 B1 | 11/2003 | Bhullar et al. |
| 6,654,625 B1 | 11/2003 | Say et al. |
| 6,656,702 B1 | 12/2003 | Yugawa et al. |
| 6,676,995 B2 | 1/2004 | Dick et al. |
| 6,689,411 B2 | 2/2004 | Dick et al. |
| 6,707,554 B1 | 3/2004 | Miltner et al. |
| 6,716,620 B2 | 4/2004 | Bashir et al. |
| 6,719,887 B2 | 4/2004 | Hasegawa et al. |
| 6,723,371 B2 | 4/2004 | Chih-Lui |
| 6,746,582 B2 | 6/2004 | Heller et al. |
| 6,749,740 B2 | 6/2004 | Funderburk et al. |
| 6,764,581 B1 | 7/2004 | Forrow et al. |
| 6,776,888 B2 | 8/2004 | Yamamoto et al. |
| 6,777,243 B2 | 8/2004 | Fukuoka et al. |
| 6,787,013 B2 | 9/2004 | Chang et al. |
| 6,800,488 B2 | 10/2004 | Khan et al. |
| 6,814,844 B2 | 11/2004 | Bhullar et al. |
| 6,818,180 B2 | 11/2004 | Douglas |
| 6,821,483 B2 | 11/2004 | Phillips et al. |
| 6,827,829 B2 | 12/2004 | Kawanaka et al. |
| 6,830,669 B2 | 12/2004 | Miyazaki et al. |
| 6,833,110 B2 | 12/2004 | Black |
| 6,841,389 B2 | 1/2005 | Novikov et al. |
| 6,856,125 B2 | 2/2005 | Kermani |
| 6,860,978 B2 | 3/2005 | Yamanishi et al. |
| 6,863,800 B2 | 3/2005 | Karinka |
| 6,881,322 B2 | 4/2005 | Tokunaga et al. |
| 6,881,550 B2 | 4/2005 | Phillips et al. |
| 6,881,551 B2 | 4/2005 | Heller |
| 6,939,450 B2 | 9/2005 | Karinka et al. |
| 7,008,799 B1 | 3/2006 | Zimmer et al. |
| 7,041,206 B2 | 5/2006 | Gephart et al. |
| 7,050,843 B2 | 5/2006 | Shartle et al. |
| 7,727,467 B2 | 6/2010 | Burke et al. |
| 7,829,023 B2 | 11/2010 | Burke et al. |
| 7,892,849 B2 | 2/2011 | Burke et al. |
| 2001/0028032 A1 | 10/2001 | Church et al. |
| 2001/0042683 A1 | 11/2001 | Musho et al. |
| 2001/0052470 A1 | 12/2001 | Hodges et al. |
| 2001/0053535 A1 | 12/2001 | Bashir et al. |
| 2001/0054319 A1 | 12/2001 | Heller et al. |
| 2001/0055784 A1 | 12/2001 | Noda et al. |
| 2002/0004196 A1 | 1/2002 | Whitson |
| 2002/0019707 A1 | 2/2002 | Cohen et al. |
| 2002/0043471 A1 | 4/2002 | Ikeda et al. |
| 2002/0044890 A1 | 4/2002 | Black |
| 2002/0053523 A1 | 5/2002 | Liamos et al. |
| 2002/0072784 A1 | 6/2002 | Sheppard, Jr. et al. |
| 2002/0081588 A1 | 6/2002 | De Lumley-woodyear et al. |
| 2002/0082797 A1 | 6/2002 | Deweese et al. |
| 2002/0084196 A1 | 7/2002 | Liamos et al. |
| 2002/0092612 A1 | 7/2002 | Davies et al. |
| 2002/0100685 A1 | 8/2002 | Huang et al. |
| 2002/0102739 A1 | 8/2002 | Nomura et al. |
| 2002/0112969 A1 | 8/2002 | Hodges et al. |
| 2002/0125145 A1 | 9/2002 | Ohara et al. |
| 2002/0133064 A1 | 9/2002 | Ueno et al. |
| 2002/0137200 A1 | 9/2002 | Takahashi et al. |
| 2002/0137230 A1 | 9/2002 | Nadaoka et al. |
| 2002/0139692 A1 | 10/2002 | Tokunaga et al. |
| 2002/0148739 A2 | 10/2002 | Liamos et al. |
| 2002/0157948 A2 | 10/2002 | Liamos et al. |
| 2002/0164822 A1 | 11/2002 | Takahashi et al. |
| 2002/0168290 A1 | 11/2002 | Yuzhakov et al. |
| 2002/0175087 A1 | 11/2002 | Hodges et al. |
| 2002/0177788 A1 | 11/2002 | Hodges et al. |
| 2002/0179440 A1 | 12/2002 | Tokunaga et al. |
| 2002/0179442 A1 | 12/2002 | Miyazaki et al. |
| 2002/0185385 A1 | 12/2002 | Charlton |
| 2002/0189941 A1 | 12/2002 | Katsuki |
| 2003/0000834 A1 | 1/2003 | Yoshioka et al. |
| 2003/0004403 A1 | 1/2003 | Drinan et al. |
| 2003/0024811 A1 | 2/2003 | Davies et al. |
| 2003/0032875 A1 | 2/2003 | Taniike et al. |
| 2003/0042137 A1 | 3/2003 | Mao et al. |
| 2003/0042150 A1 | 3/2003 | Ryu et al. |

| | | | | | | |
|---|---|---|---|---|---|---|
| 2003/0046811 | A1 | 3/2003 | Chang et al. | EP | 0 736 607 A1 | 10/1996 |
| 2003/0062263 | A1 | 4/2003 | Stanford et al. | EP | 0 740 786 B1 | 11/1996 |
| 2003/0073152 | A1 | 4/2003 | Phillips et al. | EP | 0 837 320 A3 | 4/1998 |
| 2003/0073153 | A1 | 4/2003 | Phillips et al. | EP | 0 840 122 A2 | 5/1998 |
| 2003/0088166 | A1 | 5/2003 | Say et al. | EP | 0 851 224 B1 | 7/1998 |
| 2003/0094383 | A1 | 5/2003 | Kermani | EP | 0 873 514 B1 | 10/1998 |
| 2003/0094384 | A1 | 5/2003 | Vreeke et al. | EP | 0 876 506 B1 | 11/1998 |
| 2003/0097981 | A1 | 5/2003 | Dick et al. | EP | 0 882 226 B1 | 12/1998 |
| 2003/0098233 | A1 | 5/2003 | Kermani et al. | EP | 0 887 421 A1 | 12/1998 |
| 2003/0099773 | A1 | 5/2003 | Dick et al. | EP | 0 958 495 B1 | 11/1999 |
| 2003/0100030 | A1 | 5/2003 | Nadaoka et al. | EP | 0 964 059 A2 | 12/1999 |
| 2003/0102213 | A1 | 6/2003 | Gotoh et al. | EP | 0 967 480 B1 | 12/1999 |
| 2003/0106809 | A1 | 6/2003 | Kermani et al. | EP | 0 987 544 A1 | 3/2000 |
| 2003/0109798 | A1 | 6/2003 | Kermani | EP | 1 009 850 B1 | 6/2000 |
| 2003/0132110 | A1 | 7/2003 | Hasegawa et al. | EP | 1 024 358 A1 | 8/2000 |
| 2003/0143113 | A2 | 7/2003 | Yuzhakov et al. | EP | 1 067 384 | 1/2001 |
| 2003/0146110 | A1 | 8/2003 | Karinka et al. | EP | 1 074 832 A1 | 2/2001 |
| 2003/0146436 | A1 | 8/2003 | Parker et al. | EP | 1 102 991 B1 | 5/2001 |
| 2003/0150724 | A1 | 8/2003 | Kawanaka et al. | EP | 1 119 637 B1 | 8/2001 |
| 2003/0155237 | A1 | 8/2003 | Surridge et al. | EP | 1 129 211 B1 | 9/2001 |
| 2003/0159944 | A1 | 8/2003 | Pottgen et al. | EP | 1 130 390 A1 | 9/2001 |
| 2003/0159945 | A1 | 8/2003 | Miyazaki et al. | EP | 1 156 324 A1 | 11/2001 |
| 2003/0164293 | A1 | 9/2003 | Hodges et al. | EP | 1 1152 239 A1 | 11/2001 |
| 2003/0175841 | A1 | 9/2003 | Watanabe et al. | EP | 1 225 448 A2 | 7/2002 |
| 2003/0175946 | A1 | 9/2003 | Tokunaga et al. | EP | 1 235 069 A1 | 8/2002 |
| 2003/0176183 | A1 | 9/2003 | Drucker et al. | EP | 1 236 995 A1 | 9/2002 |
| 2003/0180183 | A1 | 9/2003 | Fukuoka et al. | EP | 1 256 798 A1 | 11/2002 |
| 2003/0187338 | A1 | 10/2003 | Say et al. | EP | 1 260 589 A2 | 11/2002 |
| 2003/0188427 | A1 | 10/2003 | Say et al. | EP | 1 275 732 A1 | 1/2003 |
| 2003/0199744 | A1 | 10/2003 | Buse et al. | EP | 1 281 955 A1 | 2/2003 |
| 2003/0199893 | A1 | 10/2003 | Boecker et al. | EP | 11 288 654 A1 | 3/2003 |
| 2003/0201194 | A1 | 10/2003 | Heller et al. | EP | 1 308 720 A1 | 5/2003 |
| 2003/0203498 | A1 | 10/2003 | Neel et al. | EP | 1 312 919 A2 | 5/2003 |
| 2003/0203503 | A1 | 10/2003 | Fukuoka et al. | EP | 1 316 367 A | 6/2003 |
| 2003/0214304 | A1 | 11/2003 | Karinka et al. | EP | 1 318 396 A1 | 6/2003 |
| 2003/0217918 | A1 | 11/2003 | Davies et al. | EP | 1 324 025 A2 | 7/2003 |
| 2004/0005721 | A1 | 1/2004 | Tanike et al. | EP | 1 324 038 A2 | 7/2003 |
| 2004/0016642 | A1 | 1/2004 | Miyazaki et al. | EP | 1 327 881 A1 | 7/2003 |
| 2004/0020777 | A1 | 2/2004 | Miyamoto et al. | EP | 1 352 611 A1 | 10/2003 |
| 2004/0067166 | A1 | 4/2004 | Karinka et al. | EP | 1 352 969 A1 | 10/2003 |
| 2004/0094432 | A1 | 5/2004 | Neel et al. | EP | 1 369 684 A1 | 12/2003 |
| 2004/0094433 | A1 | 5/2004 | Neel et al. | EP | 1 369 687 A1 | 12/2003 |
| 2004/0096928 | A1 | 5/2004 | Hasegawa et al. | EP | 1 391 716 A2 | 2/2004 |
| 2004/0099540 | A1 | 5/2004 | Neel et al. | EP | 1 394 535 A1 | 3/2004 |
| 2004/0104131 | A1 | 6/2004 | Neel et al. | EP | 1 431 758 A | 6/2004 |
| 2004/0106941 | A1 | 6/2004 | Roe et al. | GB | 2365123 A | 2/2002 |
| 2004/0118681 | A1 | 6/2004 | Hellinga et al. | JP | 63128252 A2 | 5/1988 |
| 2004/0127818 | A1 | 7/2004 | Roe et al. | JP | 1291153 A2 | 11/1989 |
| 2004/0127819 | A1 | 7/2004 | Roe et al. | JP | 05-312761 | 11/1993 |
| 2004/0157337 | A1 | 8/2004 | Burke et al. | JP | 09-189675 | 7/1997 |
| 2004/0182703 | A1 | 9/2004 | Bell et al. | JP | 10 307119 A | 11/1998 |
| 2004/0186394 | A1 | 9/2004 | Roe et al. | JP | 11 337514 A | 12/1999 |
| 2004/0206625 | A1 | 10/2004 | Bhullar et al. | JP | 2000-81407 | 3/2000 |
| 2004/0251131 | A1 | 12/2004 | Ueno et al. | JP | 2003-511851 | 3/2003 |
| 2005/0008537 | A1 | 1/2005 | Mosoiu et al. | JP | 2003-149192 A | 5/2003 |
| 2005/0013731 | A1 | 1/2005 | Burke et al. | JP | 2004-20465 | 1/2004 |
| 2005/0016844 | A1 | 1/2005 | Burke et al. | JP | 2006-509187 A | 3/2006 |
| 2005/0019212 | A1 | 1/2005 | Bhullar et al. | WO | WO 86/07632 | 12/1986 |
| 2006/0057707 | A1 | 3/2006 | Cunningham et al. | WO | WO 89/09397 | 10/1989 |
| | | | | WO | WO 92/22669 | 12/1992 |
| FOREIGN PATENT DOCUMENTS | | | | WO | WO 94/16095 | 7/1994 |
| DE | 102 22 428 A | 12/2002 | | WO | WO 94/28414 | 12/1994 |
| EP | 0 057 110 B2 | 8/1982 | | WO | WO 94/29705 | 12/1994 |
| EP | 0 127 958 B2 | 12/1984 | | WO | WO 95/22597 | 8/1995 |
| EP | 0 034 049 B1 | 1/1985 | | WO | WO 96/07908 | 3/1996 |
| EP | 0 164 180 B2 | 12/1985 | | WO | WO 96/15454 | 5/1996 |
| EP | 0 170 375 A2 | 2/1986 | | WO | WO 96/33403 | 10/1996 |
| EP | 0 171 148 B1 | 2/1986 | | WO | WO 97/02487 | 1/1997 |
| EP | 0 186 286 B1 | 7/1986 | | WO | WO 97/15454 | 5/1997 |
| EP | 0 230 472 B2 | 8/1987 | | WO | WO 97/29847 | 8/1997 |
| EP | 0 255 291 B1 | 2/1988 | | WO | WO 97/30344 | 8/1997 |
| EP | 0 267 724 A | 5/1988 | | WO | WO 97/34140 | 9/1997 |
| EP | 0 287 883 A1 | 10/1988 | | WO | WO 97/39343 | 10/1997 |
| EP | 0 359 831 B1 | 3/1990 | | WO | WO 97/45719 | 12/1997 |
| EP | 0 383 322 B1 | 8/1990 | | WO | WO 98/30904 | 7/1998 |
| EP | 0 471 986 A | 2/1992 | | WO | WO 98/35225 | 8/1998 |
| EP | 0 537 761 A2 | 4/1993 | | WO | WO 98/55853 | 12/1998 |
| EP | 0 546 536 B1 | 6/1993 | | WO | WO 99/05516 | 2/1999 |
| EP | 0 732 406 A1 | 9/1996 | | WO | WO 99/13099 | 3/1999 |

| | | |
|---|---|---|
| WO | WO 99/13100 | 3/1999 |
| WO | WO 99/29429 | 6/1999 |
| WO | WO 99/30152 | 6/1999 |
| WO | WO 99/32881 | 7/1999 |
| WO | WO 99/39627 | 8/1999 |
| WO | WO 99/45387 | 9/1999 |
| WO | WO 99/51974 | 10/1999 |
| WO | WO 99/58709 | 11/1999 |
| WO | WO 99/64620 | 12/1999 |
| WO | WO 00/10007 | 2/2000 |
| WO | WO 00/18294 A | 4/2000 |
| WO | WO 00/19185 | 4/2000 |
| WO | WO 00/20626 | 4/2000 |
| WO | WO 00/26638 | 5/2000 |
| WO | WO 00/28068 | 5/2000 |
| WO | WO 00/33063 | 6/2000 |
| WO | WO 00/33072 | 6/2000 |
| WO | WO 00/33074 | 6/2000 |
| WO | WO 00/42422 | 7/2000 |
| WO | WO 00/60340 | 10/2000 |
| WO | WO 00/62047 | 10/2000 |
| WO | WO 00/73778 A1 | 12/2000 |
| WO | WO 00/73785 A2 | 12/2000 |
| WO | WO 00/78992 A2 | 12/2000 |
| WO | WO 01/25775 A1 | 4/2001 |
| WO | WO 01/25776 A1 | 4/2001 |
| WO | WO 01/33216 A1 | 5/2001 |
| WO | WO 01/36953 A1 | 5/2001 |
| WO | WO 01/40788 A1 | 6/2001 |
| WO | WO 01/46457 A2 | 6/2001 |
| WO | WO 01/57238 A2 | 8/2001 |
| WO | WO 01/57239 A2 | 8/2001 |
| WO | WO 01/57510 A2 | 8/2001 |
| WO | WO 01/67099 A1 | 9/2001 |
| WO | WO 01/71328 A1 | 9/2001 |
| WO | WO 01/71329 A1 | 9/2001 |
| WO | WO 01/72220 A1 | 10/2001 |
| WO | WO 01/73109 A2 | 10/2001 |
| WO | WO 01/73114 A2 | 10/2001 |
| WO | WO 01/73124 A2 | 10/2001 |
| WO | WO 01/73419 A1 | 10/2001 |
| WO | WO 01/73420 A1 | 10/2001 |
| WO | WO 01/75438 A2 | 10/2001 |
| WO | WO 01/84133 A1 | 11/2001 |
| WO | WO 02/00112 A2 | 1/2002 |
| WO | WO 02/08750 A1 | 1/2002 |
| WO | WO 02/08753 A2 | 1/2002 |
| WO | WO 02/10728 A1 | 2/2002 |
| WO | WO 02/14535 A2 | 2/2002 |
| WO | WO 02/22855 A2 | 3/2002 |
| WO | WO 02/32559 | 4/2002 |
| WO | WO 02/49507 A1 | 6/2002 |
| WO | WO 02/50609 A2 | 6/2002 |
| WO | WO 02/054055 A1 | 7/2002 |
| WO | WO 02/057767 A1 | 7/2002 |
| WO | WO 02/057768 A1 | 7/2002 |
| WO | WO 02/057781 A2 | 7/2002 |
| WO | WO 02/058537 A2 | 8/2002 |
| WO | WO 02/067768 A2 | 9/2002 |
| WO | WO 02/070734 A1 | 9/2002 |
| WO | WO 02/071044 A1 | 9/2002 |
| WO | WO 02/078512 A2 | 10/2002 |
| WO | WO 02/078533 A2 | 10/2002 |
| WO | WO 02/086483 A1 | 10/2002 |
| WO | WO 02/097418 A1 | 12/2002 |
| WO | WO 02/103343 A1 | 12/2002 |
| WO | WO 03/005015 A1 | 1/2003 |
| WO | WO 03/012422 A1 | 2/2003 |
| WO | WO 03/014740 A1 | 2/2003 |
| WO | WO 03/014741 A1 | 2/2003 |
| WO | WO 03/029804 | 4/2003 |
| WO | WO 03/032411 A2 | 4/2003 |
| WO | WO 03/042679 A1 | 5/2003 |
| WO | WO 03/042680 A1 | 5/2003 |
| WO | WO 03/043945 | 5/2003 |
| WO | WO 03/044511 A2 | 5/2003 |
| WO | WO 03/048756 A1 | 6/2003 |
| WO | WO 03/056345 | 7/2003 |
| WO | WO 03/060154 A2 | 7/2003 |
| WO | WO 03/067252 A2 | 8/2003 |
| WO | WO 03/069304 A2 | 8/2003 |
| WO | WO 03/083469 A2 | 10/2003 |
| WO | WO 03/085372 A2 | 10/2003 |
| WO | WO 03/091717 | 11/2003 |
| WO | WO 2004/005908 A1 | 1/2004 |
| WO | WO 2004/034053 | 4/2004 |
| WO | WO 2004/113902 A1 | 12/2004 |

OTHER PUBLICATIONS

Brian A. Gregg et al., "Cross-Linked Redox Gels Containing Glucose Oxidase for Amperometric Biosensor Applications", Analytical Chemistry, Feb. 1, 1990, pp. 258-263, vol. 62, No. 3.

Cosimino Malitesta et al., "Glucose Fast-Response Amperometric Sensor Based on Glucose Oxidase Immobilized in an Electropolymerized Poly (o-phenylenediamine) Film", Analytical Chemistry, Dec. 15, 1990, pp. 2735-2740, vol. 62, No. 24.

David L. Williams et al., "Electrochemical-Enzymatic Analysis of Blood Glucose and Lactate", Analytical Chemistry, Jan. 1970, pp. 118-121, vol. 42, No. 1.

http://www.industrial-lasers.com "Industrial Laser Solutions Articles, RP shifts into gear—Micro-welding plastic" Oct. 13, 2008 (XP-002499486).

Leonard M. Tender et al.,"Electrochemical Patterning of Self-Assembled Monolayers onto Microscopic Arrays of Gold Electrodes Fabricated by Laser Ablation", Langmuir, pp. 5515-5518 (1996), vol. 12, No. 23.

M. Beyer et al., "Development and application of a new enzyme sensor type based on the EIS-capacitance structure for bioprocess control", Biosensors & Bioelectronics, 1994, pp. 17-21.

Matsuhiko Nishizawa et al., "Penicillin Sensor Based on a Microarray Electrode Coated with pH-responsive Polypyrrole", Analytical Chemistry, Nov. 1, 1992, pp. 2642-2644, vol. 64, No. 21.

N.A. Morris et al., "An Electrochemical Capillary Fill Device for the Analysis of Glucose Incorporating Glucose Oxidase and Ruthenium (III) Hexamine as Mediator", Electroanalysis, 1992, pp. 1-9, vol. 4.

Niwa, Osamu et al.; Fabrication and Characteristics of Vertically Separated Interdigitated Array Electrodes; J. Electroanal. Chem.; 1989; 291-297; 267; The Netherlands.

Richard F. Taylor et al., "An Acetylcholine Receptor-Based Biosensor for the Detection of Cholinergic Agents", Analytica Chimica Acta, 1988, pp. 131-138.

T. Boltshauser et al., "Capacitive Humidity Sensors in SACMOS Technology with Moisture Absorbing Photosensitive Polyimide", Sensors and Actuators, 1991, pp. 509-512.

Tsutomu Horiuchi et al., "Limiting Current Enhancement by Self-Induced Redox Cycling on a Micro-Macro Twin Electrode", Journal of the Electrochemical Society, Dec. 1991, pp. 3549-3553, vol. 138, No. 12.

Vasile V. Cosofret et al., "Microfabricated Sensor Arrays Sensitive to pH and K+ for Ionic Distribution Measurements in the Beating Heart", Analytical Chemistry, May 15, 1995, pp. 1647-1653, vol. 67, No. 10.

W. Eberhardt et al., "Low Cost Fabrication Technology for Microfluidic Devices Based on Micro Injection Moulding", XP-002499487.

W. Pfleging et al., "Laser Patterning and Welding of Transparent Polymers for Microfluidic Device Fabrication", XP-002499485, SPIE vol. 6107 610705, pp. 1-11 (2006).

W. Preidel et al., "In vitro measurements with electrocatalytic glucose sensor in blood", Biomed. Biochem. Acta, 1989, pp. 897-903.

Koichi Aoki, "Quantitative analysis of reversible diffusion-controlled currents of redox soluble species at interdigitated array electrodes under steady-state conditions", Journal of Electroanalytical Chemistry, pp. 269-282, issue/volume vol. 256, No. 2, Elsevier Sequoia S.A., Lausanne.

TEST STRIP WITH SLOT VENT OPENING

RELATED APPLICATIONS

This application is a divisional of U.S. patent application Ser. No. 10/871,468, filed Jun. 18, 2004 now U.S. Pat. No. 7,829,023, which claims priority to U.S. Provisional Patent Application Ser. No. 60/480,397, filed Jun. 20, 2003, the entireties of which are hereby incorporated by reference.

FIELD OF THE INVENTION

The present invention relates generally to the testing of body fluids for concentration of analytes and more particularly to a test strip or biosensor for such testing.

BACKGROUND

Test strips are often used to measure the presence and/or concentrations of selected analytes in test samples. For example, a variety of test strips are used to measure glucose concentrations in blood to monitor the blood sugar level of people with diabetes. These test strips include a reaction chamber into which a reagent composition has been deposited. Current trends in test strips require smaller test samples and faster analysis times. This provides a significant benefit to the patient, allowing the use of smaller blood samples that can be obtained from less sensitive areas of the body. Additionally, faster test times and more accurate results enable patients to better control their blood sugar level.

In connection with smaller sample volumes, it is known to provide test strips having a sufficiently small reaction chamber such that sample fluid is drawn therein by capillary action, which is a phenomenon resulting from the surface tension of the sample fluid and the thermodynamic tendency of a liquid to minimize its surface area. For example, U.S. Pat. No. 5,141,868 discloses a test strip having a cavity sized sufficiently small to draw sample liquid therein by capillary action. The cavity is defined by two parallel plates spaced about 1 mm apart by two epoxy strips extending lengthwise along lateral sides of the plates. The cavity is open at both ends, one of which receives the sample, and the other of which allows air to escape. The cavity includes an electrode structure and carries a coating of a material appropriate to the test to be performed by the test strip.

Various other test strip designs include capillary cavities that draw sample fluid therein and include vent openings to allow air to escape. Typically, the vent opening is punched or otherwise formed in either the top or bottom film that forms the sample receiving cavity. Manufacturing issues arise because of the need to precisely locate the vent hole relative to the cavity. For example, if the cavity is centrally disposed lengthwise within the test strip, a vent hole aligned left or right of center may not connect or communicate with the cavity. Since the strips are typically mass-produced from a continuous web, an error in alignment of the vent hole can affect hundreds or even thousands of test strips.

Moreover, punching a hole for the vent opening requires a separate process step and a cutting die or other equipment to form the opening. In view of cavity sizes becoming increasingly smaller in modern test strips, forming the vent opening has become a more delicate process step. It would be desirable to reduce the potential for error and to reduce the costs associated with forming the vent opening in test strips requiring the same.

SUMMARY OF THE INVENTION

The present invention provides a test strip with a covering layer having a novel slot. The slot divides the covering layer into two parts and provides a vent opening that allows air to escape a cavity or sample receiving chamber formed in the test strip as fluid enters it. In preferred embodiments, the covering layer is clear, such that the user can see through it and the slot doubles as a "fill line." The user can thus watch the fluid sample enter the test strip, progress through the capillary cavity, and then stop at the slot or fill-line. This provides positive assurance to the user that the sample size is sufficient and the test strip has been filled properly. Advantageously, the inventive test strips can be mass-produced without having to align the slot laterally with respect to the test strip and without having to punch a vent opening.

In one form thereof, the present invention provides a test strip comprising a covering layer overlying a base substrate. The base substrate has a reagent layer disposed on it that reacts with the fluid sample and produces a measurable response that can be correlated to the concentration of the analyte being measured. The covering layer includes a chamber cover and a body cover having a slot therebetween. The slot is positioned over the reagent layer. A sample receiving chamber is disposed between the base substrate and the covering layer, and the slot communicates with the sample receiving chamber. The slot defines a vent opening in the covering layer that allows air to escape as fluid enters the sample receiving chamber.

Preferably, the slot comprises a gap which forms a space between the body cover and the chamber cover, although the covering layer can be of unitary construction, with the slot forming a recess or groove in the bottom thereof. The slot can also be formed by having one of the chamber cover and body cover overlap the other. In all cases, the slot is preferably straight and extends across the width of the covering layer, oriented substantially perpendicular to the lengthwise or longitudinal axis of the test strip. This configuration of the slot provides advantages in mass-producing the test strips, as described below.

In another preferred form, the test strip includes a spacing layer disposed between the covering layer and the base substrate. The spacing layer includes a void that further defines the height, perimeter and length of the sample receiving chamber between the base substrate and the covering layer. That is, the sample receiving chamber is bounded on its sides by vertical walls created by the void, on its top by the covering layer, and on its bottom by a reagent layer that preferably overlies the base substrate. The void is shaped as an elongate channel that begins at a fluid receiving opening at an edge of the test strip, extends along the lengthwise direction of the strip, and terminates at a location that is substantially aligned with the vent opening or slot.

The chamber cover is preferably sized to overlie substantially the entire length of the sample receiving chamber, whose length is established by the length of the void in the spacing layer, as just discussed. The interior end of the chamber cover, which corresponds to the location of the slot, is substantially aligned with the interior end of the sample receiving chamber. In this configuration, the air space defined by the slot and the air space occupied by the interior end of the sample receiving chamber connect, or overlap, such that the sample receiving chamber is in communication with the slot or vent opening, and a means for air to escape the sample receiving chamber is provided. Thus, the sample receiving chamber communicates with ambient air from the fluid receiving opening at one end and from the vent opening at its other end. The small size of the sample receiving chamber produces a capillary effect that quickly draws fluid sample therein, displacing air through the vent opening. In preferred embodiments, the slot is formed as a gap and at least a portion of the air displaced exits from the top of the test strip.

Electrodes are preferably formed on the base substrate and are disposed in the sample receiving chamber. As noted above, a reagent layer is disposed in the sample receiving chamber and covers at least one, and preferably both, electrodes. More preferably, the reagent layer extends under the spacing layer and is actually sandwiched between the spacing layer and the base substrate, extending to the lateral edges of the test strip. The reagent layer thus defines most or all of the bottom surface of the sample receiving chamber. This reagent stripe configuration provides advantages in manufacturing, as described in further detail below.

Another preferred aspect of the inventive test strips involves the chamber cover being transparent or translucent above the sample receiving chamber. Fluid entering the sample receiving chamber is thus visible through the chamber cover. Further, before the test strip has been used, the sample receiving chamber is empty and the bottom thereof is visible through the chamber cover. If the inventive test strips are used for testing blood as the fluid sample, for example, it is desirable to color the reagent layer a color that contrasts the red color of blood.

The spacing layer is preferably formed of an opaque color that contrasts with both the color of the fluid sample and that of the reagent layer. Thus, when viewed from the top of the test strip, the user sees through the transparent chamber cover and sees the color of the floor of the sample receiving chamber bounded by the contrasting color of the spacing layer. Alternatively, the contrasting color may be provided, e.g., by printing on the transparent chamber cover. A blood sample is deposited at the fluid receiving opening at the edge of the strip and is quickly drawn into the sample receiving chamber. The user can easily watch the red colored blood moving into the sample receiving chamber against the contrasting background, which provides a positive indication to the user that a sufficient size sample of blood was provided.

In another preferred aspect of the present invention, at least the underside of the chamber cover is hydrophilic, which promotes quick wicking of the sample into the elongated chamber at least as far as the vent opening. By contrast, the body cover is hydrophobic, and since the body cover defines an edge of the slot, it prevents fluid sample from wicking beyond the slot or vent opening. These contrasting hydrophobic and hydrophilic properties result in the sample fluid being quickly drawn into the sample receiving chamber, yet fluid movement is quickly halted when the sample reaches the area in the chamber that is aligned with the slot. When the slot is substantially straight, the sample forms a corresponding straight terminal edge aligned therewith. When combined with the transparent chamber cover and other preferred features noted above, the user is thus provided with a clearly defined and visible "fill line" corresponding to the slot. The user can watch the fluid sample quickly enter the sample receiving chamber and then stop at the fill line, confirming that the sample size was sufficient and that the test strip was filled properly.

In another preferred form, contact pads are formed on the base substrate at a meter insertion end of the test strip and electrode traces extend along the base substrate and connect the electrodes to the contact pads. The covering and/or spacer layer described above preferably covers most of the length of the test strip, but terminates short of the meter insertion end, thereby exposing the contact pads at the meter insertion end of the strip. This allows the contact pads to mate with corresponding electrical connections in a meter that reads the test strips.

In another form thereof, the present invention provides a method of mass producing the novel test strips described above. In this inventive method, a web of base substrate material is provided. A plurality of electrode sets is formed on the web. In preferred embodiments, the electrode sets are formed by laser ablation, more preferably, by broad field laser ablation. A series of cavities is also formed in the web. In a preferred embodiment, the cavities are formed by providing a continuous web of spacing layer material having the shape of the cavities cut out and spaced equidistantly. Each one of the cavities is aligned with a respective one of the electrode sets.

A reagent layer is provided and covers at least one electrode of each electrode set. In a preferred form, the reagent layer is applied to the web before the cavities are formed, such that the reagent layer can be applied in a continuous "stripe" of uniform thickness. Finally, a covering layer preferably made from two pieces is placed over and laminated to the web such that the two pieces are separated by a gap and the gap is positioned over the series of cavities. Preferably, both pieces of the covering layer are applied at the same time. The web is then cut into the plurality of test strips.

As noted above, this mass production method avoids the need to align the vent opening laterally relative to the test strips. Moreover, the inventive method is further advantageous because it avoids the need to otherwise form an aperture in the covering layer or base layer. The method is also well-suited to mass production of the test strips by roll processing techniques, as described herein.

In one form thereof, the present invention provides a test strip comprising a covering layer overlying a base substrate. The base substrate has a reagent layer disposed on it. The covering layer includes a chamber cover and a body cover having a slot therebetween. The body cover is thicker than the chamber cover. A sample receiving chamber is disposed between the base substrate and the covering layer, and the slot communicates with the sample receiving chamber. The slot defines a vent opening in the covering layer that allows air to escape as fluid enters the sample receiving chamber.

Advantageously, a thicker body cover absorbs more of the pressure or force imparted to the web as the assembly is rewound and stored during processing. Thus, if any adhesive squeezes out of the web as it is rewound, the adhesive will typically squeeze out around the body cover and not the chamber cover. This reduces the possibility of the adhesive squeezing out from under the chamber cover during roll processing and entering the capillary zone where it could degrade or destroy the test strips ultimately produced.

The present invention provides a very easy-to-dose test strip and provides a robust but flexible manufacturing process. The various other features that characterize the invention are pointed out with particularity in the attached claims. For a better understanding of the invention, its advantages, and objectives obtained therefrom, reference should be made to the drawings and to the accompanying description, in which there is illustrated and described preferred embodiments of the invention.

BRIEF DESCRIPTION OF THE DRAWINGS

Referring now to the drawings, wherein like reference numerals and letters indicate corresponding structure throughout the several views.

DESCRIPTION OF THE PREFERRED EMBODIMENTS

Figure 1:
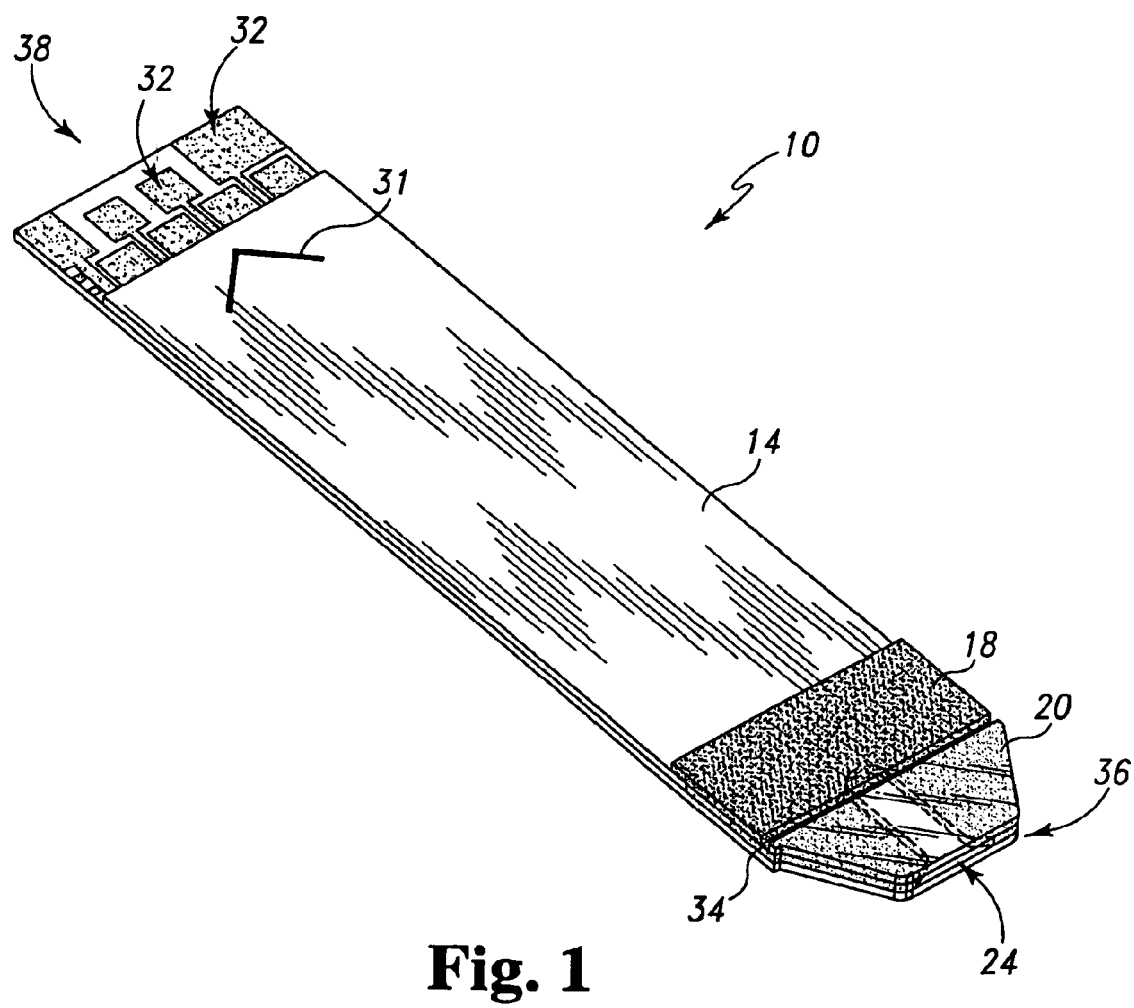
FIG. 1 is a perspective view of a test strip or biosensor in accordance with the present invention.

For the purposes of promoting an understanding of the principles of the invention, reference will now be made to the specific embodiments illustrated herein and specific language will be used to describe the same. It will nevertheless be understood that no limitation of the scope of the invention is thereby intended. Any alterations and further modifications in the described processes or devices, and any further applications of the principles of the invention as described herein, are contemplated as would normally occur to one skilled in the art to which the invention relates.

System

The present invention relates to a system that is useful for assessing an analyte in a sample fluid. The system includes devices and methods for evaluating the sample fluid for the target analyte. As more fully described hereafter, the evaluation may range from detecting the presence of the analyte to determining the concentration of the analyte. The analyte and the sample fluid may be any for which the test system is appropriate. For purposes of explanation only, a preferred embodiment is described in which the analyte is glucose and the sample fluid is blood or interstitial fluid. However, the present invention clearly is not so limited in scope.

Sensor

One component of the system is an electrochemical sensor including a sample-receiving chamber for the sample fluid, and a suitable reagent for producing an electrochemical signal in the presence of the test analyte. The sensor preferably comprises a disposable test strip, particularly one having a laminar construction providing an edge opening which communicates with the sample-receiving chamber. The reagent is disposed within the sample-receiving chamber in position to provide the electrochemical signal to a working electrode also positioned within the chamber. In appropriate circumstances, such as for glucose detection, the reagent may contain an enzyme and optionally a mediator.

Meter

The sensor is used in combination with a meter for determination of the analyte in the sample fluid. The meter conventionally includes a connection with the electrodes of the sensor and circuitry to evaluate the electrochemical signal corresponding to the concentration of the analyte. The meter may also include means for determining that the sample fluid has been received by the sensor, and that the amount of sample fluid is sufficient for testing. The meter typically will store and display the results of the analysis, or may alternatively provide the data to a separate device.

Analyte—Characteristic

The system can provide either a qualitative or quantitative indication for the analyte. In one embodiment, the system indicates simply the presence of the analyte in the sample fluid. The system may also provide a reading of the quantity or concentration of the analyte in the sample fluid. In a preferred embodiment, it is a feature of the present invention that a highly accurate and precise reading of the analyte concentration is quickly obtained from a small volume of sample fluid.

Analyte—Type

The system is useful for the determination of a wide variety of analytes. The test strip, for example, is readily adapted for use with any suitable chemistry that can be used to assess the presence of the analyte. Most preferably, the system is configured and used for the testing of an analyte in a biological fluid. Such analytes may include, for example, glucose, cholesterol, HDL cholesterol, triglycerides, lactates, lactate dehydrogenase, alcohol, uric acid, and 3-hydroxybutric acid (ketone bodies). Commensurate modifications to the system will be apparent to those skilled in the art. For purposes of explanation, and in a particularly preferred embodiment, the system is described with respect to the detection of glucose in a biological fluid.

Interferants

Test methodologies may be variously affected by the presence of interferants in the sample fluid. For example, the testing for glucose in a blood sample may be impacted by such factors as oxygen, bilirubin, hematocrit, uric acid, ascorbate, acetaminophen, galactose, maltose, and lipids. The present system is adaptable to minimize or eliminate the adverse effects of interferants that may also be present in the sample fluid. These effects may be addressed by appropriate selection of test materials and parameters, such as by the selection of chemistries that are known to be impacted less, or not at all, by possible interferants. As is known in the art, other steps may also be taken to address possible interferant effects, such as the use of coatings or films that prevent the interferant from entering the test zone. In addition, modifications to the electrode configurations or interrogation methods can be used to minimize the effect of interferants.

Fluid Type

The system is useful with a wide variety of sample fluids, and is preferably used for the detection of analytes in a biological fluid. In this context, the term "biological fluid" includes any bodily fluid in which the analyte can be measured, for example, interstitial fluid, dermal fluid, sweat, tears, urine, amniotic fluid, spinal fluid and blood. The term "blood" in the context of the invention includes whole blood and its cell-free components, namely plasma and serum. In addition, the system is useful in connection with control fluids that are used in conventional fashion to verify the integrity of the system for testing.

In a preferred embodiment, the system is employed for the testing of glucose. The sample fluid in this instance may specifically include, for example, fresh capillary blood obtained from the finger tip or approved alternate sites (e.g., forearm, palm, ear lobe, upper arm, calf and thigh), fresh venous blood, and control solutions supplied with or for the system.

The fluid may be acquired and delivered to the test strip in any fashion. For example, a blood sample may be obtained in conventional fashion by incising the skin, such as with a lancet, and then contacting the test strip with fluid that appears at the skin surface. It is an aspect of the present invention that the test strip is useful with very small fluid samples. It is therefore a desirable feature of the invention that only a slight incising of the skin is necessary to produce the volume of fluid required for the test, and the pain and other concerns with such method can be minimized or eliminated.

It is also well known that different locations on the skin will produce more or less amounts of blood upon lancing. The finger tip, for example, is a commonly used site for obtaining a blood sample because it produces a relatively large amount of blood upon lancing. However, it is also known that areas that produce larger volumes of blood are generally associated with greater degrees of pain for the user. It is therefore an additional advantage of the present system that the required volume of sample fluid is sufficiently small that the test strip is useful with the amount of blood typically obtained upon lancing less productive, but also less painful, areas of the skin, such as the palm and upper arm. The use of these locations to obtain sample fluids for testing is sometimes referred to as "alternate site testing". The present invention is particularly well suited to use with sample fluids, e.g., blood or interstitial fluid, obtained at these alternate sites.

Test Strip—General
Introduction.

The test strip includes several basic components. The strip comprises a small body defining a chamber in which the sample fluid is received for testing. This "sample-receiving chamber" is filled with the sample fluid by suitable means, preferably by capillary action, but also optionally assisted by pressure or vacuum. The sample-receiving chamber includes electrodes and chemistry suitable for producing an electrochemical signal indicative of the analyte in the sample fluid.

Basic Description.

Referring in particular to the drawings, there is shown a preferred embodiment of a test strip useful in accordance with the present invention. The test strip 10 includes a base substrate 12, a spacing layer 14 and a covering layer 16 comprising body cover 18 and chamber cover 20. The spacing layer 14 includes a void portion 22 to provide a sample-receiving chamber 24 extending between the base substrate 12 and the covering layer 16.

The base substrate 12 carries an electrode system 26 including a plurality of electrodes 28 and electrode traces 30 terminating in contact pads 32. The electrodes are defined as those portions of electrode traces 30 that are positioned within the sample-receiving chamber 24. Various configurations of the electrode system 26 may be used, as set forth hereafter. A suitable reagent system 33 overlies at least a portion of the electrodes or electrode pairs 28 within the sample-receiving chamber.

The body cover 18 and the chamber cover 20 overlying the spacing layer 14 define a slot 34 therebetween, the slot defining a vent opening communicating with the sample-receiving chamber to allow air to escape the chamber as a sample fluid enters the chamber from the edge opening or fluid receiving opening 35. The test strip therefore includes a dosing end 36 and a meter insertion end 38. The shape of the dosing end is typically distinguishable from the meter end so as to aid users. In addition, strip graphics are preferably used to further improve the intuitiveness of the strip design; e.g., arrow 31 indicates the direction of insertion of the strip into the meter.

General Dimensions.

The test strip is a relatively small device that is dimensioned for compactness and ease of storage and use. In a typical embodiment, the strip length is on the order of 20 to 50 mm, preferably about 33 to about 38 mm, in length, and 5 to 15 mm, preferably about 7 to about 9 mm, in width. The distance from the slot or vent opening 34 to the edge of the meter is sized to provide a "grab area" where there is no blood present, and to guard against blood contamination of the meter contact area, and therefore may be in the range of 5 to 35 preferably $\geq 13$ mm The length of the test strip portion (from the meter insertion end 38) that is inserted into the meter is preferably 6.0 mm along the long axis of the test strip.

The preferred laminar construction of the test strip also provides a device that is relatively thin. The minimal thickness of the strip allows ready packaging of the strip in appropriate containers that are convenient for the user. For example, the overall thickness of the test strip may be about 500 to 525 µm. The thickness of the test strip portion that is inserted into the meter contact may be about 250 µm.

Substrate

The test strip includes a base substrate 12 which comprises an insulating material supporting the electrode system and other components. Typically, plastics such as vinyl polymers, polyimides, polyesters, and styrenes provide the electrical and structural properties which are required. Further, because the test strip is preferably mass producible from rolls of material, it is desirable that the material properties be appropriate to have sufficient flexibility for roll processing, while also giving a useful stiffness to the finished strip. The base substrate can be selected as a flexible polymeric material such as polyester, especially high temperature polyester materials; polyethylene naphthalate (PEN); and polyimide, or mixtures of two or more of these. Polyimides are available commercially, for example under the trade name Kapton®, from E.I. duPont de Nemours and Company of Wilmington, Del. (duPont). A particularly preferred base substrate material is MELINEX® 329 available from duPont.

Electrodes
Type.

The invention relates to an "electrochemical sensor", which is a device configured to detect the presence of, and/or measure the concentration of, an analyte by way of electrochemical oxidation and reduction reactions within the sensor. These reactions are transduced to an electrical signal that can be correlated to an amount or concentration of the analyte. The test strip therefore includes an electrode system 26 comprising a set of measuring electrodes, e.g., at least a working electrode and a counter electrode, within the sample-receiving chamber. The sample-receiving chamber is configured such that sample fluid entering the chamber is placed in electrolytic contact with both the working electrode and the counter electrode. This allows electrical current to flow between the measuring electrodes to effect the electrooxidation or electroreduction of the analyte.

In the context of the present invention, a "working electrode" is an electrode at which analyte is electrooxidized or electroreduced with or without the agency of a redox mediator. The term "counter electrode" refers herein to an electrode that is paired with the working electrode and through which passes an electrochemical current equal in magnitude and opposite in sign to the current passed through the working electrode. The term "counter electrode" is meant to include counter electrodes which also function as reference electrodes (i.e., counter/reference electrodes).

Electrode Material.

The working and counter electrodes, and the remaining portions of the electrode system, may be formed from a variety of materials, as known in the art. The electrodes should have a relatively low electrical resistance and should be electrochemically inert over the operating range of the test strip. Suitable conductors for the working electrode include gold, palladium, platinum, carbon, titanium, ruthenium dioxide, and indium tin oxide, and iridium, as well as others. The counter electrode may be made of the same or different materials, e.g., silver/silver chloride. In a preferred embodiment, the working and counter electrodes are both gold electrodes.

Electrode Application.

The electrodes may be applied to the base substrate in any fashion that yields electrodes of adequate conductivity and integrity. Exemplary processes are well known in the art, and include, for example, sputtering, printing, etc. In a preferred embodiment, gold electrodes are provided by coating the base substrate and then removing selected portions of the coating to yield the electrode system. A preferred removal method is laser ablation, and more preferably broad field laser ablation, as disclosed in U.S. patent application Ser. No. 10/601,144, filed on Jun. 20, 2003, entitled Method of Making a Biosensor, the disclosure of which is hereby incorporated by reference.

Laser ablative techniques typically include ablating a single metallic layer or a multi-layer composition that includes an insulating material and a conductive material, e.g., a metallic-laminate of a metal layer coated on or laminated to an insulating material (discussed below). The metallic layer may contain pure metals, alloys, or other materials, which are metallic conductors. Examples of metals or metallic-like conductors include: aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys or solid solutions of these materials. Preferably, the materials are selected to be essentially unreactive to biological systems; such materials include: gold, platinum, palladium, iridium, silver, or alloys of these metals or indium tin oxide. The metallic layer may be any desired thickness. In a preferred embodiment, the thickness is about 500 nm.

Configuration.

The electrode system may have a variety of configurations suited to the operation of the test strip and meter. For any embodiment, the working and counter electrodes preferably are positioned and dimensioned to minimize the volume of sample fluid required to cover them. It is also preferable that the electrodes be configured to maintain a current flux of sufficient magnitude as to be measurable using a relatively inexpensive hand-held meter.

By way of further example, a preferred embodiment includes a counter electrode which extends around both sides of the working electrode. The counter electrode therefore has two elements, one in front of the working electrode and the other behind the working electrode, as the sample fluid enters the sample-receiving chamber. More specifically, the counter electrode includes elements 40 and 42 which extend across the sample-receiving chamber. Each of these elements is about 250 µm wide. The working electrode element 44 has a width of about 250 µm, and is spaced from each of the two counter electrode elements by about 255 µm. It will be appreciated that this is only one of a number of configurations for the measuring electrodes.

The traces 30 and the contact pads 32 may be provided in a variety of fashions consistent with their intended function relative to the test strip. These components of the electrode system are preferably composed of the same material as the electrodes, and are preferably applied to the base substrate in the same manner and simultaneously with the application of the electrodes. In a preferred embodiment, the traces and contact pads are gold, and are formed by laser ablation, particularly as described in U.S. patent application Ser. No. 10/601,144, filed on Jun. 20, 2003, entitled Method of Making a Biosensor, the disclosure of which is hereby incorporated by reference. However, alternate materials and methods of application may be employed.

Chemistry

Reagent Composition.

The test strip includes a chemical reagent within the sample-receiving chamber for reacting with the test analyte to produce the electrochemical signal that represents the presence of the analyte in the sample fluid. The reagent layer can include a variety of active components selected to determine the presence and/or concentration of various analytes. The test chemistry is therefore selected in respect to the analyte to be assessed. As is well known in the art, there are numerous chemistries available for use with each of various analytes. For example, in one preferred embodiment, the test strip of the present invention can include one or more enzymes, co-enzymes, and co-factors, which can be selected to determine the presence of glucose in blood. The selection of an appropriate chemistry is therefore well within the skill in the art, and further description herein is not required in order to enable one to make and use the test strips with various analytes.

Adjuvants.

In conventional fashion, the reagent chemistry may include a variety of adjuvants to enhance the reagent properties or characteristics. For example, the chemistry may include materials to facilitate the placement of the reagent composition onto the test strip and to improve its adherence to the strip, or for increasing the rate of hydration of the reagent composition by the sample fluid. Additionally, the reagent layer can include components selected to enhance the physical properties of the resulting dried reagent layer, and the uptake of a liquid test sample for analysis. Examples of adjuvant materials to be used with the reagent composition include thickeners, viscosity modulators, film formers, stabilizers, buffers, detergents, gelling agents, fillers, film openers, coloring agents, and agents endowing thixotropy.

In a preferred embodiment of the test sample, the majority of the chamber is hollow before use. In the very small sample chamber of the test strips according to the present invention, it is preferable that the reagent layer be thin and uniform.

Since the sample-receiving chamber is very small, less than about 1 µl, the depth or vertical height of the chamber is small. Consequently, the reagent layer should not occupy the majority of the internal cavity of the chamber. The reagent layer should be sufficiently thin to leave ample space for the test sample in the chamber. Further, the liquid test sample will hydrate or dissolve the thin reagent layer more quickly. As discussed in the above reaction scheme, the mediator and mediator redox products diffuse through and within the reagent layer/gradient to the electrodes. The reactive components and intermediates will have a short distance to diffuse through a thin reagent, therefore, diffusion to the electrodes will occur in less time. Additionally, the capture efficiency of mediator redox products at an electrode will be greater for a thin layer of enzyme than a thick layer.

Conversely, a thick reagent layer will take more time for the liquid test sample to hydrate or dissolve, and a thick reagent layer will increase the time that it takes for the mediator/mediator redox products to approach the electrodes. This can delay the time to determine the analyte concentration and introduce errors into the determination.

It is preferred that the reagent layer have a uniform thickness. Thickness inhomogeneity can lead to variability in determining the analyte concentration. In a preferred embodiment, the reagent layer has a uniform thickness throughout the entire sample receiving chamber. In this preferred embodiment, the reagent layer is not thicker around the perimeter of the sample receiving chamber adjacent the vertical side walls that define the chamber than in the central portion of the chamber. Consequently, the reagent layer does not exhibit a meniscus profile.

The reagent composition is formulated as a viscous solution that can be deposited in a thin, uniform layer on the base layer. The reagent composition includes thickeners and thixotropic agents to enhance the physical properties of the reagent layer. The thickeners are selected to provide a thick, liquid matrix having the remaining components homogeneously dispersed therein. The thickening and thixotropic agents also inhibit the liquid or semi-paste material from running or spreading over the surface of the base layer after it has been deposited and before it dries. After the reagent composition is deposited, it quickly dries to a readily hydratable matrix.

The reagent composition is provided to dry rapidly either with air drying or heat drying. After drying, the deposited reagent layer exhibits a thickness of between about 1 micron and about 20 microns. More preferably, the dried reagent layer exhibits a thickness of between about 2 microns and about 6 microns.

The reagent composition can be deposited on the test strip surface using a variety of coating methods including curtain coating, hot melt coating, rotary screen coating, doctor blade or air knife coating, Meyer bar coating, and reverse roll coating techniques. These techniques are known to those skilled in the art. Preferably, the reagent layer is deposited on the flexible web as a wet composition at a thickness of between about 40 µm and about 100 µm. More preferably, the reagent composition is deposited as a wet composition at a thickness of between about 60 µm and about 80 µm. The composition may be applied as a uniformly thin layer of a reagent directly on top of the measuring electrodes and along the length of a web of multiple test strips, as a continuous narrow band. In preferred embodiments, the narrow band has a width of between about 7 mm and 8 mm and a dry thickness of between about 3 um and about 20 um. The composition may also be applied onto other electrodes that may reside in the sample-receiving chamber, depending on the desired functionality of such extraneous electrodes.

Spacing Layer

Configuration.

The test strip includes a spacing layer 14 which overlies the base substrate and which in part defines the sample-receiving chamber. In particular, the spacing layer 14 includes a void portion 22 substantially defining the height and the perimeter of the sample-receiving chamber 24. The void portion 22 is conveniently placed to have an edge opening whereby the sample fluid is contacted with the edge opening to enter into the sample-receiving chamber. The edge opening preferably is located at the end of the test strip, although it will be appreciated that placement on a side edge is also useful.

Materials.

The spacing layer 14 may be made of any material useful for fabrication with the test strip. Because the spacing layer partially defines the height of the sample-receiving chamber, the material should have sufficient strength at thicknesses appropriate to the desired height of the chamber. Another function of the spacing layer is to protect the electrode traces that extend along the upper surface of base substrate 12. The material should also be readily attached to the base substrate and the cover materials, either by heat-sensitive or pressure-sensitive adhesives, or other means such as heat or laser welding. Examples of suitable materials include a 100 µm PET, PEN foil coated or combined with adhesives such as ARCare 90132 from Adhesives Research Inc.

Covering Layer

Configuration.

A covering layer 16 is received over and attached to the spacing layer 14. One function of the covering layer is to form the top surface of the sample-receiving chamber. Another function is the provision of a hydrophilic surface to aid in acquisition of the test sample. In addition, the covering layer 16 preferably defines a vent opening 34 that allows air to escape from the interior of the chamber as the sample fluid enters and moves into the sample-receiving chamber.

Figure 1A:
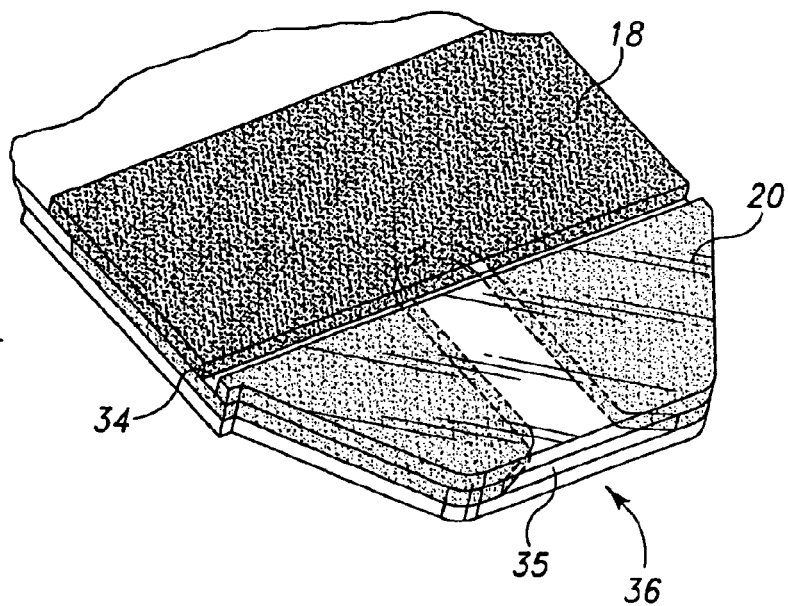
FIG. 1A is an enlarged fragmentary perspective view of the test strip shown in FIG. 1, illustrating one embodiment of the novel vent opening or slot.
Figure 1B:
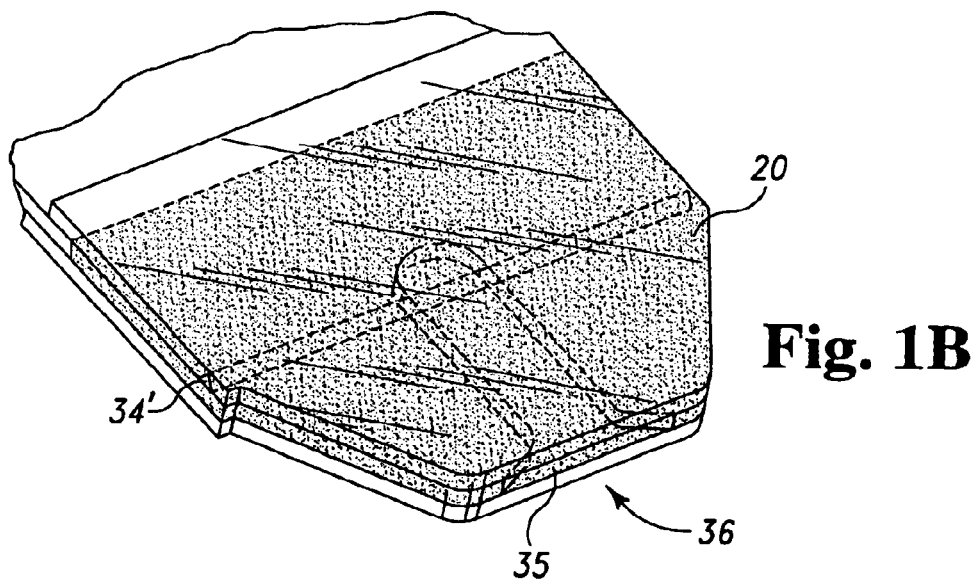
FIG. 1B is an enlarged fragmentary perspective view illustrating an alternate embodiment of the vent opening or slot in accordance with the present invention.

The covering layer can be formed as a unitary piece with slot 34' formed as a recess on the underside thereof, as shown in FIG. 1B. For mass production purposes, slot 34' would be substantially straight as shown and extend across the entire width of the test strip, such that air would vent from the sample receiving chamber 24 to the vent openings formed on opposite lateral sides of the test strip. However, the slot could comprise a groove or recess that only extends from the chamber 24 to one side of the test strip, although such configuration is not preferred for mass production purposes.

Figure 1C:
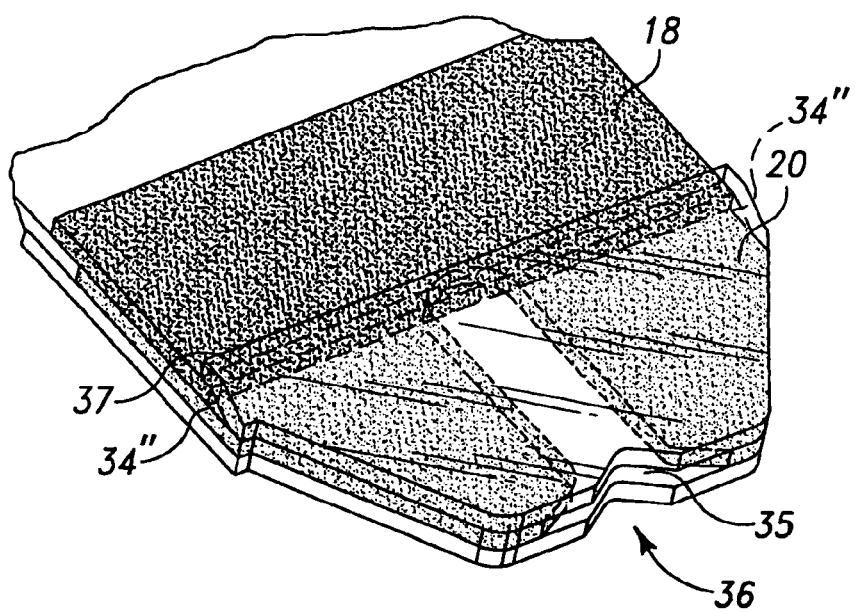
FIG. 1C is an enlarged fragmentary perspective view illustrating another alternate embodiment of the vent opening or slot and also illustrating an alternate configuration of the opening to the sample receiving chamber of the biosensor in accordance with the present invention.

Another alternate embodiment is shown in FIG. 1C, in which chamber cover 20 "overlaps" body cover 18. In this arrangement, a small end portion 37 of cover layer 20 is bent upwardly and extends across the edge of body cover 18. A slot 34" is thereby formed having roughly a triangular shaped cross section as can be seen at the edges of the strip, at which there are triangular shaped openings that allow air to escape. In this "overlap" arrangement, the precise placement of the chamber cover 20 with respect to body cover 18 along the lengthwise direction of the strip is not critically important. That is, the amount of chamber covering material overlapping body cover 18 can vary without affecting the dimensions or placement of the slot. This has advantages in manufacturing, as will become apparent with reference to the discussion below.

Preferably, body cover 18 and chamber cover 20 comprise two separate members for ease in fabrication and in forming the vent opening. Body cover 18 and chamber cover 20 are both disposed in substantially the same horizontal plane. The chamber cover 20 substantially covers the void portion 22 of the spacing layer, and forms the top of the sample-receiving chamber. The chamber cover preferably includes a hydrophilic coating or treatment 21 on its underside, as described in more detail below. The body cover and the chamber cover are positioned end to end in the lengthwise direction along the test strip and include slot 34 therebetween as shown in FIG. 1A. The slot is located adjacent the interior end of the void portion 22 of the spacing layer, and in the preferred embodiment in FIG. 1A, forms a small gap that spaces chamber cover 20 from body cover 18. The gap constitutes the vent opening 34 in communication with the sample-receiving chamber. Slot 34 is substantially straight and extends across the width of test strip 10. Slot 34 is oriented substantially perpendicular to the longitudinal or lengthwise axis of test strip 10. Sample fluid entering the sample-receiving chamber will expel air through the vent opening defined by slot 34. If the slot be formed as a gap, some or most of the air expelled will exit from the top of the test strip.

The slot is located at a position relative to the sample-receiving chamber that is interior of the location of the electrode system 26. Sample fluid entering the sample-receiving chamber will progress as far as the vent opening, but no further. When viewed from the top, the slot provides a visual indication of a "fill-line," as described herein. The placement of the vent opening therefore assures that sufficient sample fluid can be received to fully cover the electrode system. At the same time, the placement of the vent opening will inhibit continued wicking of the sample fluid beyond the region of the electrode system.

The formation of the slot and vent opening by the spacing of the body cover and the chamber cover is further advantageous because it avoids the need to otherwise form an aperture in the covering layer or base layer. In the prior art, it has been an approach to form the vent opening by punching a hole in either the top or bottom film forming the sample-receiving chamber, which presents fabrication issues because of the need to precisely locate the hole relative to the sample-receiving chamber. While this approach is also suitable for a test strip, the preferred design described herein avoids the need to align the vent opening laterally relative to the test strip. Further, the present design is well suited to mass production of the test strips by roll processing techniques, as described hereafter.

Figure 3:
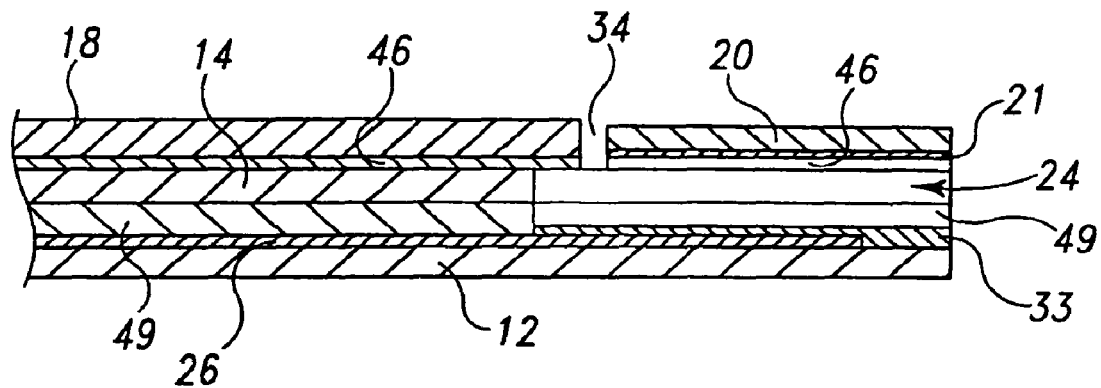
FIG. 3 is a cross-sectional view of a portion of the biosensor of FIG. 1, additionally illustrating adhesive layers that have been omitted from FIGS. 1-2.
Figure 4:
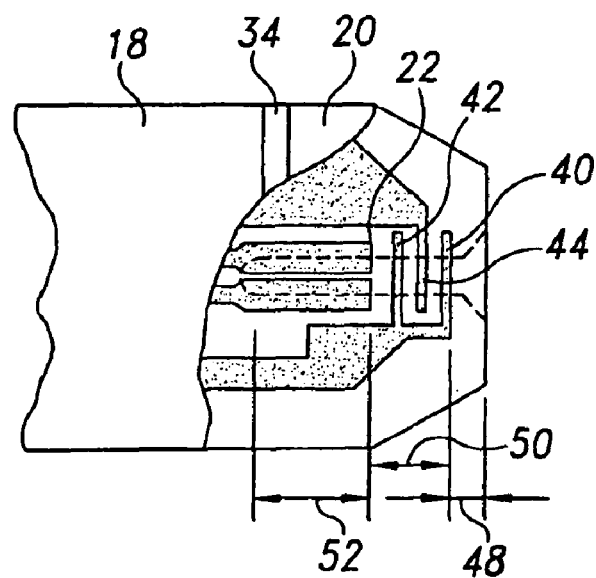
FIG. 4 is a top, plan view of a portion of the biosensor of FIG. 1, with portions broken away to show underlying details.

At the same time, the vent construction may be made in a manner to inhibit the wicking of sample fluid laterally along the slot beyond the middle area that overlies the sample receiving chamber 24. For example, the body cover is preferably secured to the spacing layer by means of an adhesive 46, as shown in FIG. 3. The use of a hydrophobic adhesive will inhibit blood, interstitial fluid, and other aqueous liquids from moving along the laterally-extending slot by capillary action. The entire body cover, or portions adjacent to the vent opening, may also be hydrophobic to inhibit wicking. Materials and methods for providing hydrophobic properties for a surface of a material are well known in the art. The chamber cover may be secured to the spacing layer by the same or different adhesive than adhesive 46, as explained below.

Figure 2:
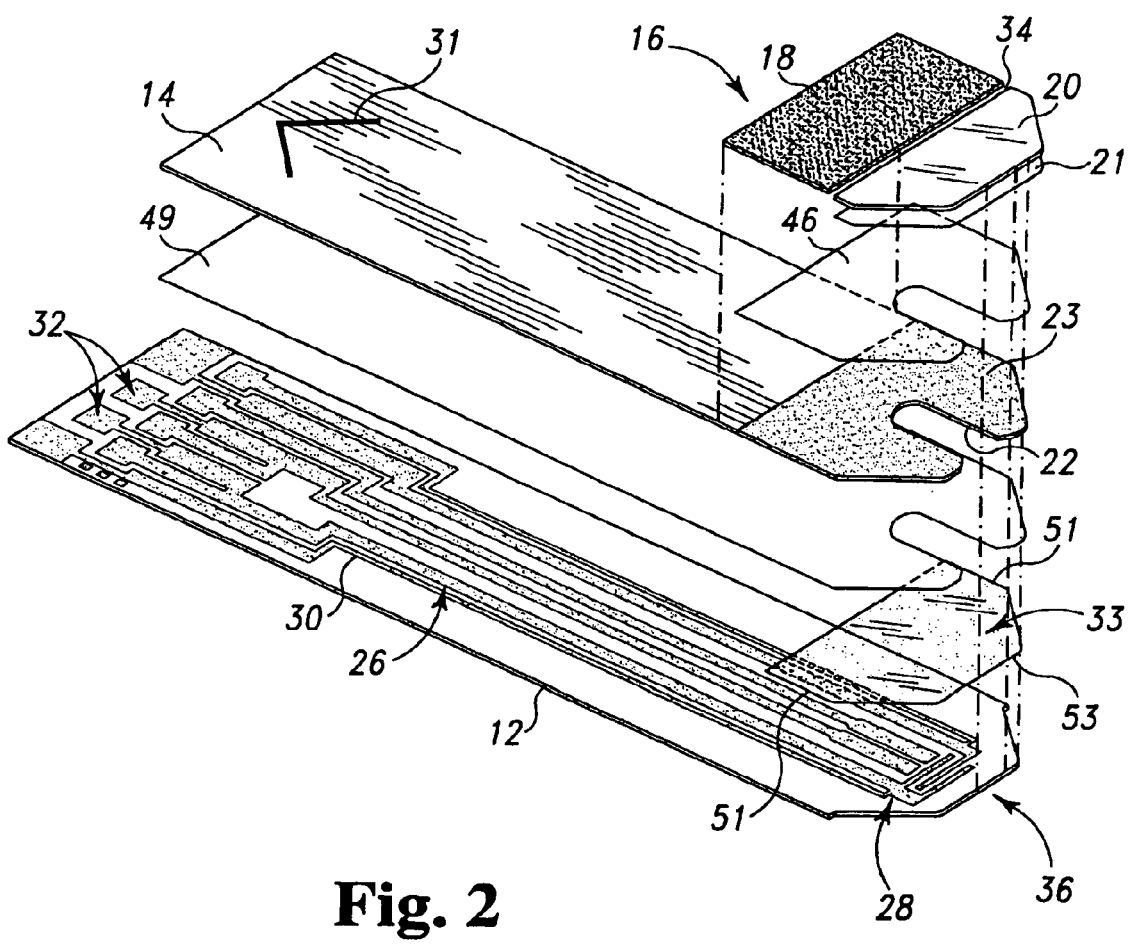
FIG. 2 is an exploded, perspective view of the biosensor of FIG. 1.

Adhesive 49 secures the spacing layer to the base substrate 12. Adhesive 46, as well as adhesive 49 and the material for spacing layer 14, are all formed of hydrophobic material in the illustrated embodiment. As such the vertical walls of the capillary chamber formed in strip 10 are hydrophobic. By contrast, the floor of the chamber is covered with a hydrophilic reagent and the underside of layer 20 is coated with a hydrophilic coating 21 (FIG. 2). In other words, the horizontal surfaces in the capillary are hydrophilic while the vertical surfaces are hydrophobic. This has been found to promote good wicking of the sample into the capillary chamber, yet prevents unwanted migration of the sample laterally from the chamber, e.g., between the spacer layer and the base substrate.

Materials.

The body cover and chamber cover may be made of any materials useful for fabrication with the test strip. The materials for the body cover and the chamber cover may be the same or different. The materials should be readily attached to the spacing layer, either by heat-sensitive or pressure-sensitive adhesives, or other means such as heat or laser welding. Examples of suitable materials for both the chamber cover and body cover include approximately 127 µm thick foil of PET. The chamber cover preferably includes a hydrophilic layer 21 as disclosed in WO 02/085185, ARFlow® 90191 from Adhesives Research Inc.

The covering layer 16 may also be used to facilitate viewing of the sample fluid as it enters the sample-receiving chamber. This is accomplished by providing a contrast in color or shading between the chamber and the surrounding area. For example, in one approach the portion of the spacing layer 14 that surrounds void 22 is provided with a color that contrasts with the color of the bottom of the sample-receiving chamber, e.g., the color of the chemical reagent layer positioned at the bottom of the chamber. This contrasting color may be provided, for example, by the application of an ink or other coloring agent to the portions of the spacing layer adjacent the sample-receiving chamber. A colored section 23 of layer 14 is pictured in FIG. 2. The chamber cover 20 is then provided as a transparent or translucent material that allows the user to view the chamber and the adjacent spacing layer. As sample fluid enters from the edge of the test strip, the user is able to observe its progress as it moves by capillary action toward the vent opening. This type of feature is further described in U.S. Pat. No. 5,997,817, issued to Crismore et al. on Dec. 7, 1999, and is hereby incorporated by reference.

Capillary

The sample-receiving chamber formed by the base substrate, spacing layer and chamber cover essentially comprises several sections into which the sample fluid will travel. A first, entry section 48 extends from the edge opening to the area of the measuring electrode system. A second, test section 50 extends through the area of the electrode system. A third section 52 extends from the measuring electrode system to the vent opening. It will be appreciated that the testing of the sample fluid occurs in the area of the electrode system in the test section. However, the sample fluid will also fill the other sections of the chamber in the course of filling the test strip.

Dimensions.

The height and width of the sample-receiving chamber are selected based upon a variety of considerations, including the fluid being tested and the analyte at issue. For example, the chamber dimensions are preferably sized to promote capillary flow of the test fluid into the chamber. Preferred chamber heights for use with blood, for example, are from about 50 µm to about 200 µm, and most preferably from 120 to 180 µm. In a preferred embodiment, the chamber height is about 150 µm. The width of the chamber may similarly be selected to match a desired sample fluid and analyte. For example, the chamber should be sufficiently wide to expose a desired amount of the working and counter electrodes, and should be narrow enough to avoid the requirement of an undue amount of sample fluid for testing. The width of the sample-receiving chamber and the width of the working electrode define the area of the working electrode. The area represents a further design consideration as it relates to signal amplitude and instrumentation design.

Volume.

The sample-receiving chamber is preferably provided as having a minimal volume, in order to reduce the amount of sample fluid needed for conducting a test. The overall sample-receiving chamber, including all of the three sections extending from the edge opening to the vent opening, has a total volume that can be considered to be a factor of the area of the chamber from the edge to the vent, and the height of the chamber from the base substrate to the chamber cover 20. However, the "net chamber volume" comprises the volume of sample fluid required to fill this space. The net chamber volume of the sample-receiving chamber will be the equivalent of the total chamber volume less the volume occupied by the electrodes, the reagent, and perhaps other items such as a sorbent material, if included.

As previously indicated, the volume of the overall sample-receiving chamber is comprised of the volumes attributable to the three sections of the chamber. Each of the sections is generally sized to be as small as practical for the operation of the test strip. However, there are considerations, and possibly other functions, that will impact on the size of each section.

The chamber volumes are a factor of both height and area. The height is a result of the thickness of the spacing layer and the thickness of the adhesives used to secure the spacing layer to the other layers. For example, the base substrate and the chamber cover are attached to opposite sides of the spacing layer. One method of attachment is the heat or laser sealing of the materials. It is preferred, however, to attach these layers by the use of suitable adhesives, such as heat-sensitive or pressure-sensitive adhesives. In this approach, the height of the sample-receiving chamber, i.e., the distance between the facing surfaces of the bottom substrate and the chamber cover, will be impacted by the thickness of the adhesive layers. As shown in FIG. 3, chamber 24 is bounded on its bottom side by reagent layer 33 and its top side by chamber cover 20. However, adhesive layers 46 and 49 as well as spacing layer 14 define the total height of chamber 24.

Further, in a preferred embodiment, the reagent layer 33 extends between base substrate 12 and spacing layer 14 and indeed extends the entire width of the test strip, as described below. The height of the chamber may therefore also be increased due to the presence of the reagent layer underlying the spacing layer. In this embodiment, and if adhesive is employed, it has been found that the adhesive may combine with the test reagent, at least to an extent that causes the adhesive to fill somewhat into and around the reagent. The heights of the reagent and adhesive layers therefore are not necessarily additive in the final test strip. Rather, the height of the resulting space between the base substrate and the spacing layer is somewhat less than the combination of the heights of the separate reagent and adhesive layers prior to lamination.

It has also been found that the combination of the adhesive and the reagent advantageously helps to create a seal along the edge of the sample-receiving chamber. This inhibits sample fluid from wicking into the reagent material present in the space between the base substrate and the spacing layer in the time frame necessary for performing a test.

The first entry section is available to receive the sample fluid and direct it to the measuring electrodes. This section can be quite small in size, and may comprise only a short segment of the chamber. The length of this section is preferably less than 1200 μm.

The second testing section includes the test or measuring electrodes, and is also sized to require a minimal volume of sample fluid. A primary factor controlling the size of this second section will be the type, number, size, signal strength, and configuration of the measuring electrodes. The length of this section is preferably about 1260 μm. A preferred volume is about 0.265 μL, based on a capillary height of 0.15 mm, and a capillary width of 1.4 mm.

The sample fluid moves past the measuring electrodes and into the third section. This provides assurance, and preferably allows for specific confirmation, that the measuring electrodes are properly wetted. This confirmation may be by visual observation by the user, or by automatic detecting means. For example, dose sufficiency electrodes may be placed in this section to detect when the sample fluid has progressed into this section to a point that the wetting of the measuring electrodes is assured. This can be used as a trigger for initiating the application of the potential to the electrodes. The length of this section is preferably 50 to 500 μm, and more preferably 255 to 400 μm. The volume is preferably 0.01 to 0.1 μL, and more preferably 0.05 to 0.08 μL.

In a preferred embodiment, the overall net chamber volume of the sample-receiving chamber is less than about 1 μL, and is more preferably less than about 0.5 μl. Desirable ranges for the net chamber volume of the sample-receiving chamber include volumes from about 0.15 to about 1.4 μL, more preferably from about 0.4 to about 0.7 μl.

Sorbent.

The sample chamber may be otherwise empty, which is preferred, or may alternatively include a sorbent material. Suitable sorbent materials include polyester, nylon, cellulose, and cellulose derivatives such as nitrocellulose. A sorbent material could be included to facilitate the uptake of the sample fluid by assisting in wicking the fluid into the chamber. The use of a sorbent material would also serve to further reduce the void volume of the sample-receiving chamber for reception of the sample fluid.

Fill Method.

The preferred method of filling the sample chamber is by capillary action. In addition, the filling of the test strip can be augmented by other means, such as applying a pressure on the sample fluid to push it into the sample chamber, and/or creating a vacuum on the sample chamber to pull the sample fluid into the chamber.

Hydrophilic Coating.

For purposes of capillary filling of the sample-receiving chamber, various approaches are available to facilitate the movement of the sample fluid into the chamber. For example, any or all of the surfaces defining the chamber may be selected or treated to improve hydrophilicity. Such treatment may comprise the use of known hydrophilic materials, application of a hydrophilic material onto the surface, or treatment of the surfaces to increase hydrophilicity, as described below. In addition, the reagent composition may be formulated to be readily hydrated and to encourage filling of the sample-receiving chamber. As previously indicated, a sorbent may also be used.

Testing for Analyte

The electrochemical sensor is operated by applying a suitable potential or series of potentials across the working and counter electrodes, and across the dose sufficiency electrodes. When a mediator is used, the magnitude of the required potential across the working and counter electrodes will be dependent on the redox mediator. Moreover, the potential at the electrode where the analyte is electrolyzed is typically large enough to drive the electrochemical reaction to or near completion, but the magnitude of the potential is preferably not large enough to induce significant electrochemical reaction of interferants. For glucose, for example, an applied potential difference typically is between about +100 mV and about +550 mV when using a DC potential. When using AC potentials these can be typically be 5 to 100 mV RMS.

A potential may be applied before or after the sample begins to enter the sample-receiving chamber. However, a potential is preferably applied after the sample has entered the chamber, and more preferably after it has been determined that there is a sufficient amount of sample in the sample-receiving chamber for conducting a test. The timing of the application of a potential may be triggered in a variety of fashions, including visual observation by the user, a time delay following sampling of the fluid to the test strip, or upon electrical or other automated detection of a sufficient amount of sample fluid in the chamber. The visual and electrical alternatives also may act as redundant failsafes to assure proper operation of the device. Preferably, the test strip and system utilize separate detecting means, such as dose sufficiency electrodes, for determining when the fluid sample has sufficiently filled the chamber.

When a potential is applied and the sample fluid is in the sample-receiving chamber, an electrical current will flow between the working electrode and the counter electrode. The current can be a result of the electrolysis of the analyte in the sample fluid when a potential of sufficient magnitude is applied. In this case electrochemical reaction occurs via the redox mediator, generally as previously described. In the case where small amplitude potential is applied, particularly in the case of AC potentials, the current is produced not necessarily by electrolysis, but by ionic motion and response of the dielectric in the sample chamber. Those skilled in the art will recognize that there are many different reaction mechanisms that will achieve the same result.

Control Solution

A test may be applied to the test strip after dosing to confirm that a control solution, and even that the correct control solution, has been administered. The control solutions aid the user in confirming that the entire system is functioning within design specifications, and that the test strips have not been stored improperly or otherwise mistreated. Acceptable strips will recover values within specified tolerance ranges for the particular strip lot being tested. The tolerance ranges in question will be published for each strip lot on the container label.

Method of Making Strip

In a preferred embodiment, the sensor comprises a multi-layered, laminate test strip and a covering layer 16. These components may be assembled in various ways. For example, the components may be assembled by use of adhesives, heat sealing, laser welding, and a variety of other suitable techniques appropriate for securing the adjacent materials. The test strips are preferably assembled in a large number on a single sheet or web, and the strips are thereafter separated for storage and use.

The laminate test strip may be assembled sequentially by successively laying down one layer at a time. Alternatively, the test strip can be prepared by assembling and processing individual components or layers, which are then laminated together to provide the functional test strip. In one preferred form, two or more basic components of the test strip are prepared simultaneously. Then in one or a series of assembly or laminating steps, the basic components are combined to produce the test strip, which may or may not require further processing. In a preferred embodiment, the test strip is assembled from three basic components: a metallized substrate preferably with a reagent layer coated on metallic electrodes defined on the substrate, a spacing layer having a cavity preformed therein, and one or more top or cover layers.

With such small dimensions for the sample-receiving chamber, the characteristics of the reagent layer can have a significant impact on the operation of the test strip, particularly in view of hydration and mixing characteristics. The reproducibility of the quantity, location, thickness and other properties of the reagent layer is therefore important. It is therefore desirable for the composition to include materials which specifically enhance the physical characteristics, such as the uniformity and flatness, of the applied layer.

In one particular aspect, the test strip includes a unique manner of incorporating the reagent. The reagent is placed in the sample-receiving chamber at least on the working electrode, and preferably also on the counter electrode. The reagent may be applied to the test strip in a variety of fashions as is well understood in the art. In a preferred embodiment, the reagent composition is applied as a thin coating over the electrodes supported on the base substrate.

More particularly, the reagent is placed onto the base substrate in a manner that positions the reagent composition between the base substrate and the spacing layer. This manner of application helps to make the reagent layer more flat and uniform in thickness. In contrast, a procedure of the prior art has been to first prepare the reaction well or cavity, and to then fill the reagent into the well. However, this can result in a more uneven reagent layer due to phenomena such as the formation of a meniscus at the perimeter of the well. This in turn can cause the reagent to have a different thickness adjacent to the side walls of the reaction well than in the interior portion, which can cause inconsistency in the filling of the chamber, prolonged dissolution intervals, and inconsistent mixing of the reagent with the sample fluid, and the ultimate test results. By placing the reagent onto the base substrate before the spacing layer is added, there is no meniscus effect to disrupt the even layering of the reagent as it dries on the base substrate. In addition, this method of application facilitates the mass production of the test strips.

Referring to the drawings, the test strip 10 is shown as including a reagent layer 33 that extends between the bottom substrate 12 and the spacing layer 14. More particularly, the reagent forms a layer 33 which covers both the top surface of the bottom substrate 12 and the electrodes 28. The reagent covers at least the working electrode, and preferably also the counter electrode. In the most preferred embodiment, the reagent layer extends the full width of the test strip. The reagent layer also preferably extends from the end edge to the vent opening. The reagent layer thus extends under the spacing layer and is sandwiched between the spacing layer and the base substrate.

The reagent composition is applied to the bottom or base substrate in any suitable fashion that provides a desired and uniform layer which will ultimately extend under the spacing layer. The reagent is preferably applied in a continuous coating directly onto the bottom substrate, and onto the electrodes received thereon. As described hereafter, the reagent composition is most preferably applied in the course of producing a large quantity of test strips on a webbing of material. In this manner, the reagent may be applied in the way of a continuous stripe of material that extends over a substrate roll that is later separated into individual test strips. The reagent composition is allowed to dry or otherwise set up and the spacing layer is applied thereover.

In a related aspect, a preferred manner of securing the spacing layer to the bottom substrate is the use of an adhesive. In addition to securing the layers together, it has been found that the adhesive will sufficiently engage with the reagent composition as to help to seal the space between the bottom substrate and the spacing layer. The adhesives preferably placed on the spacing layer, which is laminated onto the base substrate. The adhesive thereby contacts the portion of the reagent which extends under the spacing layer.

Although the spacing layer of the illustrated embodiment is formed from Melinex® material with adhesives on both sides thereof, it is also possible to form spacing layer 14 as a continuous adhesive material, such as a double-sided tape.

In a further aspect, a preferred embodiment is described in which the analyte is glucose. In the case of glucose, the active components of the reagent composition will typically include an oxidoreductase, such as an enzyme for glucose; optionally a co-enzyme or co-factor; and a redox mediator. These components are typically dissolved or suspended in a matrix. The liquid test sample hydrates or dissolves the matrix, and the analyte diffuses through the matrix to react with one or more of the active components. Typically, the enzyme oxidizes the glucose in the test sample to gluconolactone and/or gluconic acid. The mediator, in turn, reacts with or oxidizes the reduced enzyme, and consequently the mediator is reduced in the process. The reduced mediator can be detected at one of the electrodes on the test strip.

In a specific example of an oxidation/reduction reaction scheme useful for detecting glucose in human blood, a test sample containing glucose reacts with an enzyme such as Glucose-Di-Oxidoreductase (Gluc-Dor), and optionally a co-enzyme or cofactor such as pyrrolo-quinoline-quinone (PQQ), in the presence of a redox mediator. The mediator may include, for example, benzoquinone, transition metal complexes, e.g., potassium ferricyanide, osmium derivatives (e.g., osmium bipyridyl complexes such as described in WO 98/35225) and nitrosoanaline derivatives (see U.S. Pat. No. 5,286,362). This produces the oxidized form of the analyte, gluconolactone, and the reduced form of the redox mediator. The mediator thereafter shuttles the redox equivalent of mediator product, the reduced mediator, to the electrode surface by diffusion. There the mediator is oxidized quantitatively at a defined anodic potential, and the resulting current is related to the apparent glucose concentration.

A representation of the reaction sequences for this reaction system using a nitrosoaniline derivative is provided below in Equation 1.

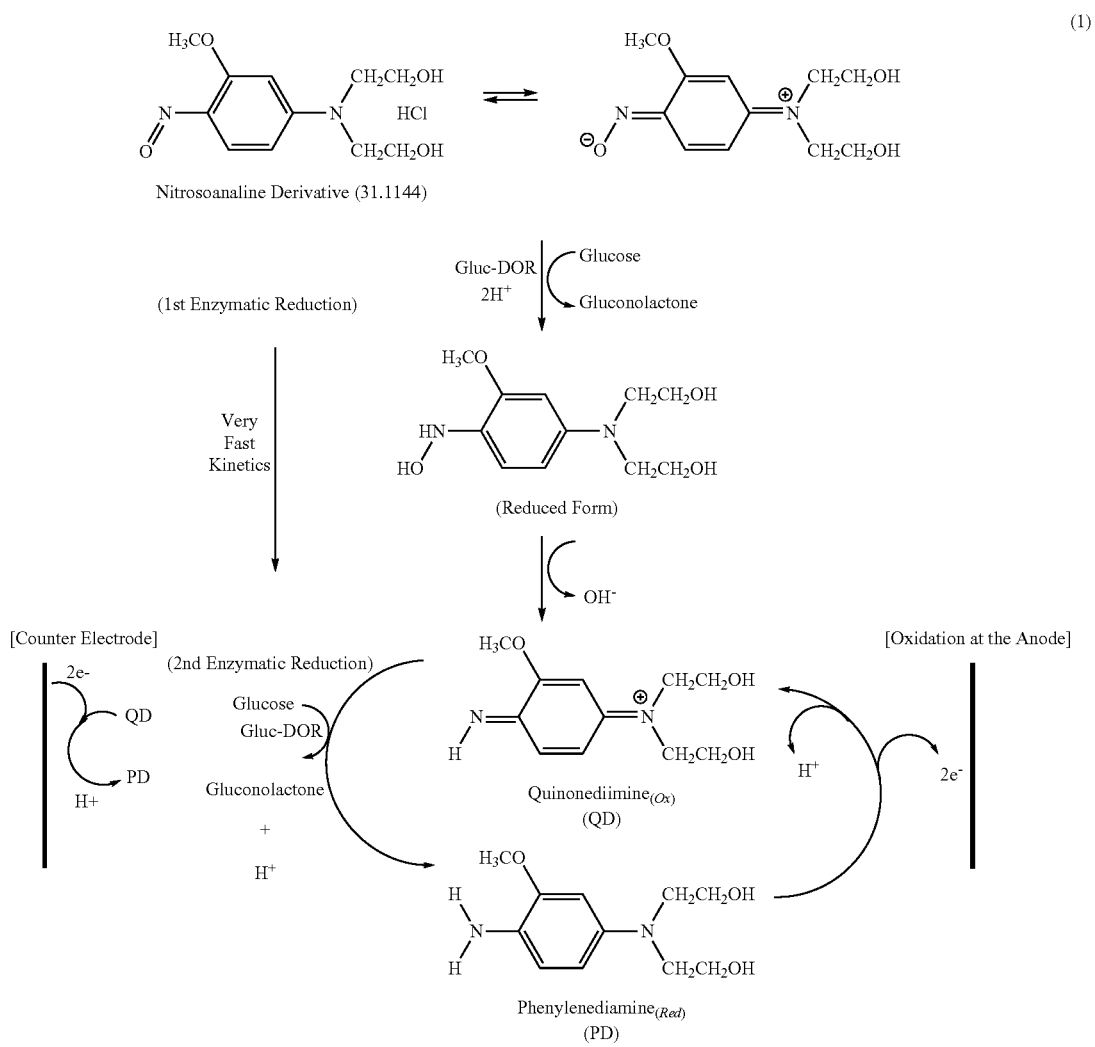

As shown, the nitrosoaniline derivative, o-methoxy-[N,N-bis-(2-hydroxyethyl)]-p-nitrosoaniline, initially exists as a mixture of two isomers, or tautomers, in equilibrium with each other. Reaction of Gluc-Dor with glucose in the test sample yields gluconolactone and the reduced form of Gluc- Dor (Gluc-Dor·2H$^+$). The reduced form of Gluc-Dor (Gluc-Dor·2H$^+$) reacts rapidly with the nitrosoaniline derivative, which is reduced and which regenerates Gluc-Dor. The reduced nitrosoaniline derivative then undergoes hydrolysis to form quinonediimine (QD). In a second enzymatic, redox reaction, Gluc-Dor reacts with glucose to yield another molecule of Gluc-Dor·2H$^+$ and gluconolactone. The Gluc-Dor·2H$^+$ reacts with (is oxidized by) quinonediimine to regenerate Gluc-Dor, and produces a phenylene diamine derivative (PD). PD is then oxidized at the working electrode to produce a current related to glucose concentration. Additionally, at the counter electrode QD can be reduced to PD.

Adjuvants.

With such small dimensions for the sample-receiving chamber, the characteristics of the reagent layer can have a significant impact on the operation of the test strip, particularly in view of hydration and mixing characteristics. The control and reproducibility of the quantity, location, width, thickness, and other properties of the reagent layer become more important as the chamber volume decreases and test time diminishes. It is therefore desirable for the composition to include materials that specifically enhance the physical characteristics, such as the uniformity and flatness, of the applied layer. Additionally, the method of application can impact the physical characteristics, control, and reproducibility of the reagent layer.

The reagent composition can therefore also include a variety of adjuvants to enhance the reagent properties or characteristics. For example, the composition may include adjunct materials to facilitate the placement of the reagent composition onto the test strip and to improve its adherence to the strip. The composition can also include materials to increase its rate of hydration and/or its increase its influence on the capillary action to fill the chamber with the test sample. Examples of adjunct materials to be used with the reagent composition include thickeners, viscosity modulators, film formers, stabilizers, buffers, detergents, gelling agents, fillers, film opening agents, coloring agents, and agents endowing thixotropy.

The adjuvant materials or components can impact the application, reproducibility and physical properties of the reagent layer. The adjunct materials can include one or more of the following:

Thickeners may include, for example, (1) starches, gums (e.g., pectin, guar gum, locust bean (carob seed) gum, konjac gum, xanthan gum, alginates, and agar), casein, gelatin, and phycocolloids; (2) cellulose and semi-synthetic cellulose derivatives (carboxymethyl-cellulose, methyl cellulose, hydroxymethylcellulose, hydroxyethylcellulose, methylhydroxyethylcellulose); (3) polyvinyl alcohol and carboxy-vinylates; and (4) bentonite, silicates, and colloidal silica. Preferred thickeners include a combination of a xanthan gum sold under the trade name Keltrol F by CP Kelco US, Inc., and carboxylmethyl cellulose sold under the trade name AQUALON® CMC 7F PH by Hercules Inc., Aqualon Division.

Film forming and thixotropic agents useful in the reagent composition include polymers and silica. Preferred thixotropic agents include silica sold under the trade name Kieselsäure Sipernate FK 320 DS by Degussa AG. Preferred film forming agents include polyvinylpyrrolidone, sold under the trademark polyvinylpyrrolidon Kollidon 25, by BASF, and polyvinyl propionate dispersion.

Stabilizers for the enzyme in the reagent can be selected from sacchhrides and mono- or di-fatty acid salts. Preferred stabilizers include trehalose sold under the trade name D-(+)-Trehalose dihydrate by Sigma Chemical Co. and sodium succinate.

Detergents can be selected from water-soluble soaps, as well as water-soluble synthetic surface-active compounds such as alkali, earth alkali or optionally substituted ammonium salts of higher fatty acids, e.g., oleic or stearic acid, mixtures of natural fatty acids, for example, from coconut or tallow oil, fatty sulphates, esters of sulphonic acids, salts of alkyl sulphonic acids taurine salts of fatty acids, fatty acid amides, and ester amides. Preferred detergents for the present invention include an ester amide, n-octanoyl-N-methylglucamide, sold under the trade name Mega-8 by Dojindo Molecular Technologies, Inc., and a fatty acid salt, N-methyl oleyl taurate sodium salt, sold under the trade name Geropon T77 by Rhodia HPCII (Home, Personal Care and Industrial Ingredients).

It should be understood that one or more of the specific additives above described can exhibit additional properties and consequently could be categorized in one or more of the classes above noted.

Mediator.

A mediator for use in the reagent composition can be selected as any chemical species (generally electroactive) which can participate in a reaction scheme involving an enzyme, an analyte, and optionally a cofactor, and reaction products thereof, to produce a detectable electroactive reaction product. Typically, participation of the mediator in the reaction involves a change in its oxidation state (e.g., a reduction), upon interaction with any one of the analyte, the enzyme, or a cofactor, or a species that is a reaction product of one of these (e.g., a cofactor reacted to a different oxidation state). A variety of mediators exhibit suitable electrochemical behavior. A mediator can preferably also be stable in its oxidized form, may optionally exhibit reversible redox electrochemistry, can preferably exhibit good solubility in aqueous solutions, and preferably reacts rapidly to produce an electroactive reaction product. Examples of suitable mediators include benzoquinone, meldola blue, other transition metal complexes, potassium ferricyanide, osmium derivatives (see WO 98/35225) and nitrosoanaline-based mediators (see U.S. Pat. No. 5,286,362). In a preferred embodiment, the reagent composition utilizes a nitrosoaniline-based chemistry.

Preferred mediators include N-(2-hydroxyethyl)-N'-p-nitrosophenyl-piperazine, N,N-bis-(2-hydroxyethyl)-p-nitrosoaniline, o-methoxy-[N,N-bis-(2-hydroxyethyl)]-p-nitrosoaniline, p-hydroxynitrosobenzene, N-methyl-N'-(4-nitrosophenyl)-piperazine, p-quinone dioxime, N,N-dimethyl-p-nitrosoaniline, N,N-diethyl-p-nitrosoaniline, N-(4-nitrosophenyl)-morpholine, N-benzyl-N-(5'-carboxypentyl)-p-nitrosoaniline, N,N-dimethyl-4-nitroso-1-naphthylamine, N,N,3-trimethyl-4-nitrosoaniline, N-(2-hydroxyethyl)-5-nitrosoindoline, N,N-bis-(2-hydroxyethyl)-3-chloro-4-nitrosoaniline, 2,4-dimethoxy-nitrosobenzene, N,N-bis-(2-methoxyethyl)-4-nitrosoaniline, 3-methoxy-4-nitrosophenol, N-(2-hydroxyethyl)-6-nitroso-1,2,3,4-tetrahydroquinoline, N,N-dimethyl-3-chloro-4-nitrosoaniline, N,N-bis-(2-hydroxyethyl)-3-fluoro-4-nitrosoaniline, N,N-bis-(2-hydroxyethyl)-3-methylthio-4-nitrosoaniline, N-(2-hydroxyethyl)-N-(2-(2-methoxyethoxy)-ethyl)-4-nitrosoaniline, N-(2-hydroxyethyl)-N-(3-methoxy-2-hydroxy-1-propyl)-4-nitrosoaniline, N-(2-hydroxyethyl)-N-(3-(2-hydroxyethoxy)-2-hydroxy-1-propyl)-4-nitrosoaniline, N-(2-hydroxyethyl)-N-(2-(2-hydroxyethoxy)-ethyl)-4-nitrosoaniline. Particularly preferred mediators according to the present invention include N,N-bis-(2-hydroxyethyl)-p-nitrosoaniline, o-methoxy-[N,N-bis-(2-hydroxyethyl)]-p-nitrosoaniline, and N-(2-hydroxyethyl)-N-(2-(2-hydroxyethoxy)-ethyl)-4-nitrosoaniline.

An exemplary reagent composition is listed below in Table I.

TABLE I

| Components | Function | Amount Abs. | % solids w/w. | Note. |
|---|---|---|---|---|
| Keltrol F | Thickener | 11.60 g | 0.24% | |
| Carboxy methylcellulose | Thickener | 27.24 g | 0.57% | |
| Kieselsäure Sipernat 320 DS | Film Opener | 97.01 g | 2.01% | |
| Polyvinylpyrrolidine PVP K25 | Film Former | 89.33 g | 1.85% | |
| Propiofan | Film Former | 257.09 | 5.34% | |
| GlucDOR | Apo-Enzyme | 19.127 g | 0.40% | 0.673 MU/g |
| pyrrolo-quinoline quinine (PQQ) | Co-Factor | 0.5329 g | 0.01% | |
| Na-Succinate | Stabilizer | 23.23 g | 0.48% | |
| Trehalose | Stabilizer | 23.6 g | 40.49% | |
| $KH_2PO_4$ | Buffer | 12.02 g | 0.39% | |
| $K_2HPO_4 \times 3\ H_2O$ | Buffer | 43.43 g | 0.90% | |
| Nitrosoaniline | Mediator | 41.26 g | 0.86% | |
| Mega 8 | Detergent | 13.23 g | 0.27% | |
| Geropon T77 | Detergent | 1.405 g | 0.03% | |
| KOH 5N | Adjust Buffer | 36.47 g | 0.76% | |
| Water total | | 4114.52 g | | |
| Sum | | 4817.80 g | | |
| Solids | | | 14.6% | |

Mixing.

The components of the reagent composition are admixed with water to provide a homogeneous, viscous suspension. The order of addition is not critical for the invention. A sufficient amount of the buffer solution is added to maintain the reagent composition at a pH of about 7. Typically the selected components are pre-mixed with water to provide a variety of stock solutions that can be combined to yield the final reagent composition. For example, a buffer solution can be prepared by combining the phosphate salts and, optionally, the sodium succinate. Other stock solutions include: the thickening agents, i.e., Keltrol F and the carboxymethyl cellulose; the surfactants, i.e., Geropon T77 and Mega 8; the enzyme and co-enzyme or cofactor; and the mediator.

The following provides an example of the preparation of a reagent composition. The reagent composition can be prepared by first preparing the following stock solutions:

| Buffer Solution pH 6.9 to 7.1 | |
|---|---|
| | Amount (gm) |
| $H_2O$ | 1214.62 |
| $KH_2PO_4$ | 18.27 |
| $K_2HPO_4$ | 43.43 |
| Na succiante | 23.23 |

| Keltrol F Solution | |
|---|---|
| | Amount (gm) |
| $H_2O$ | 287.06 |
| Buffer Solution | 101.35 |
| Keltrol F | 11.60 |

| Carboxymethylcellulose (CMC) Solution | |
|---|---|
| | Amount (gm) |
| $H_2O$ | 1334.76 |
| Na CMC[1] | 27.24 |

[1]Na CMC is a sodium salt of carboxymethyl cellulose sold by Hercules Inc., Aqualon Division Aqualon Division

| Silica Suspension | |
|---|---|
| | Amount(gm) |
| $H_2O$ | 722.99 |
| Sipernat 320[1] | |

[1]Kieselsäure Sipernat 320 DS (Silica) sold by Degussa AG.

| Polyvinylpyrrolidone (PVP) Solution | |
|---|---|
| | Amount (gm) |
| Buffer Solution | 226.03 |
| Mega 8[1] | 13.23 |
| Geropon T77[2] | 1.405 |
| PVP[3] | 89.33 |

[1]Mega 8 is n-octanoyl-N-methylglucamide sold by Dojindo Molecular Technologies Inc.
[2]Geropon T77 is N-methyl oleyl taurate sodium salt sold by Rhodia HPCII.
[3]PVP is Polyvinylpyrrolidone K25 sold by BASF.

| Trehalose Solution[1] | |
|---|---|
| | Amount (gm) |
| $H_2O$ | 36.4 |
| Trehalose | 23.6 |

[1]This trehalose solution is used only in preparing the "Enzyme Solution" listed below.

| PQQ Solution | |
|---|---|
| | Amount (gm) |
| Buffer Solution 1st addition | 101.59 |
| PQQ | 0.533 |
| Buffer Solution 2nd addition | 30.0 |

| Enzyme Solution | |
|---|---|
| | Amount (gm) |
| PQQ Solution | 132.12 |
| Gluc-Dor (673 U/mg Ly) | 19.13 |
| Trehalose Solution | 58.75 |

| Mediator Solution | |
|---|---|
| | Amount (gm) |
| Buffer Solution | 782.27 |
| Mediator | 41.26 |
| 5N KOH | 36.47 |

The buffer solution, Keltrol F solution, CMC solution, and the Silica suspension were prepared a day before. These solutions can then be combined as listed below to prepare the reagent composition.

| Final Reagent Composition | |
|---|---|
| Thickener I (Keltrol F solution) | 331.51 g |
| Thickener II (CMC Solution) | 1262.9 g |
| PVP Solution | 315.05 g |
| Silica suspension | 762.3 g |
| Propiofan solution | 257.09 g |
| Mediator Solution | 855.84 g |
| Enzyme Solution | 196.65 g |
| 5N KOH | as required to achieve final pH of 6.9 to 7.1 |
| Water (bidistilled) | 518.69 g |

For this reagent prior to coating, the final pH was 6.96 and did not need adjustment with 5N KOH solution. The measured viscosity was 111 mPas, which is in the correct range for coating of 105 to 115 mPas.

Figure 5:
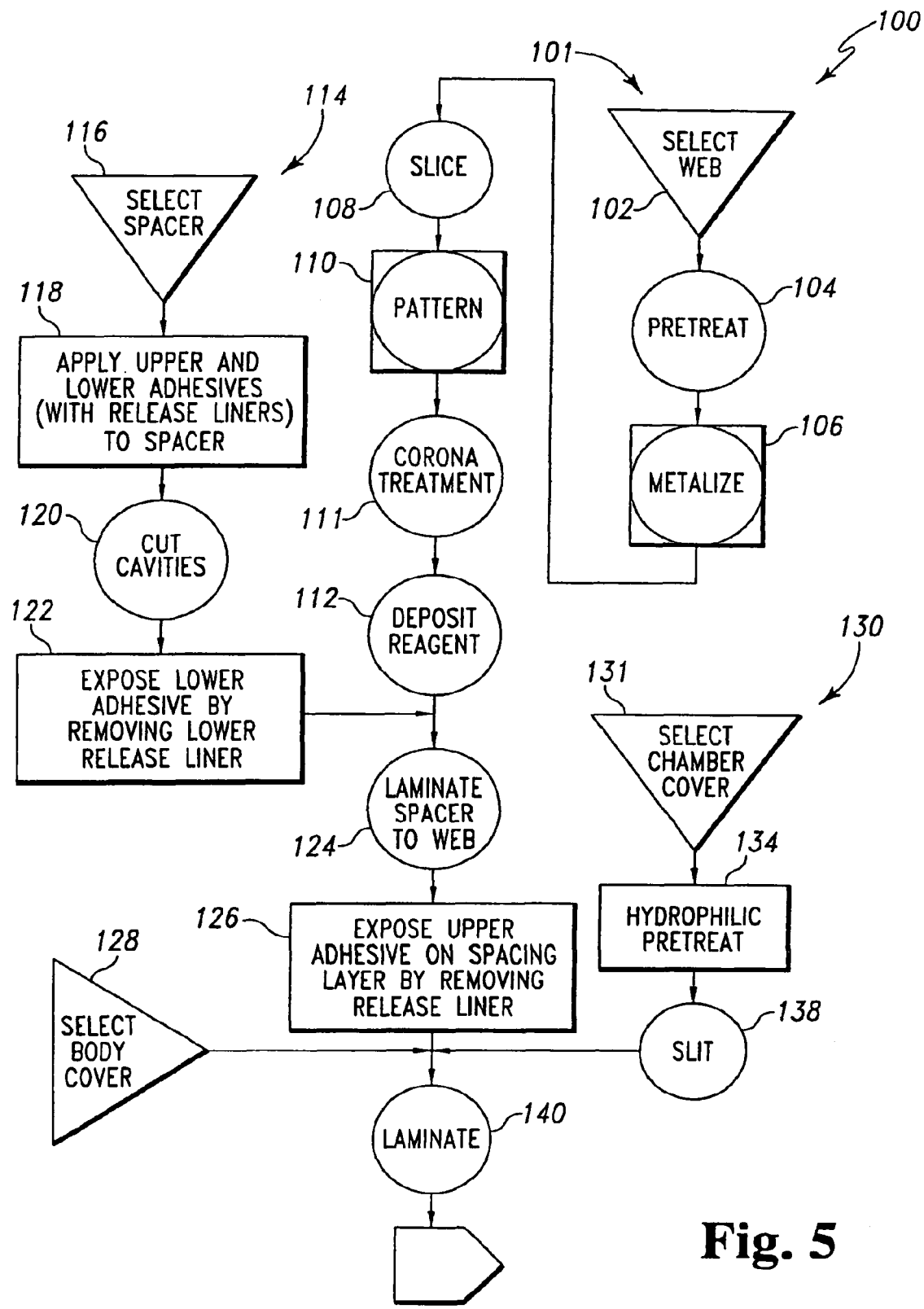
FIGS. 5 and 5A show a process flow diagram for a method for producing a biosensor in accordance with the present invention.
Figure 5A:
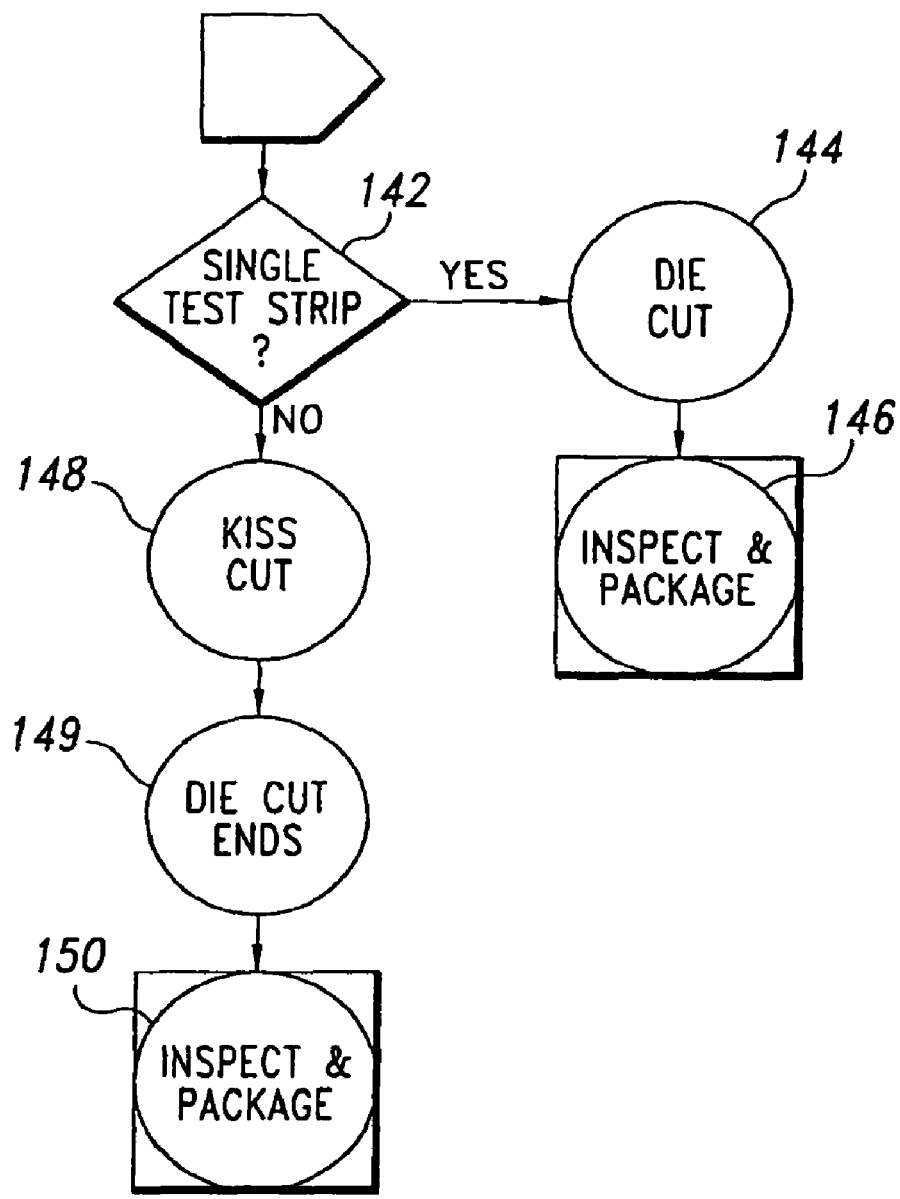

FIGS. 5 and 5A present a flow chart illustrating a preferred process 100 for preparing a test strip useful in accordance with the present invention. Process 100 begins in the central process line 101 at stage 102 with selection of a film material for the base layer or base substrate. In a preferred embodiment, the film is provided as a continuous roll having a width and length suitable for fabricating a large number of test strips. In subsequent finishing steps, the processed film can be subdivided to provide a single strip or web having a width that approximates the length of the test strip and includes a series of test strips, or can be die cut to provide individual test sensors.

From stage 102, the film proceeds to stage 104 where it is pretreated to receive a metal coating and is coated with the metal in one continuous process. The pretreatment can be used to clean or modify the surface to provide a uniform coating thickness and better adhesion of the subsequent metallized layer. The pretreatment can include subjecting the film to corona discharge or Argon plasma. Immediately after this pre-treatment, a uniform conductive coating is applied to the film as shown at 106. Alternatively, suitable substrates with metal coatings can be obtained commercially.

The metallic layer may contain pure metals, alloys, or other materials, which are metallic conductors. Examples of metals or metallic-like conductors include: aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys or solid solutions of these materials. Preferably, the materials are selected to be essentially unreactive to biological systems; such materials include: gold, platinum, palladium, iridium, or alloys of these metals. The metallic layer may be any desired thickness.

The conductive coating is preferably a metal layer that is applied by a variety of methods, including but not limited to sputtering, physical vapor deposition (PVD), plasma assisted vapor deposition (PAVD), chemical vapor deposition (CVD), electron beam physical vapor deposition (EBPVD), and/or metal-organic chemical vapor deposition (MOCVD). Vapor deposition is typically performed under vacuum. These techniques are well known in the art and can be used to selectively provide a uniformly thin coating of metal onto a substrate. The resulting metallized film can be inspected to ensure that the metal coating is uniform and free of material defects.

The roll of metallized film next encounters stage 108 where it is subdivided and/or sized to provide webs having a width that approximates the final length of an individual test strip. The slicing can be accomplished using fixed-knife slitting equipment well-known in the art.

A single web proceeds to stage 110 for patterning the electrodes, traces, and contacts or pads. At this stage, the electrodes, traces, and contact pads are formed by removing metal from the surface of the web strip. The excess metal can be removed using a variety of techniques well known in the art. At this stage, one or more indexing or registration marks can be formed either on a first edge proximate to the electrodes, the opposite second edge proximate to the electrode pad, on both edges or anywhere in between. The indexing marks, particularly those at an edge, can be used in subsequent operations to align layered components prefabricated in separate operations.

In a preferred method, the metal is laser ablated to eliminate undesired portions of the metal and leave the desired electrical components. In accordance with this method, selected areas are laser etched simultaneously, in a "broad field", as opposed to using linear movement of a focused laser beam. This broad field laser ablation method provides a precise metal pattern rapidly and at reduced cost as compared to other approaches. Corona treatment of the patterned substrate is then conducted at stage 111.

The patterned web continues on to stage 112, where a reagent layer is deposited onto the electrodes. In a preferred embodiment, the reagent layer is deposited as a continuous elongate stripe extending adjacent or close to the first edge, and overlying the measuring electrodes formed on the patterned web. As previously noted, the reagent is consequently located across the full width of the test strip, including the area laterally outside of the sample-receiving chamber and between the base substrate and the spacing layer. Also as noted, this will facilitate the drying of the reagent without discontinuities, edge effects, or other variances that would detract from providing a thin, flat, uniform reagent layer within the sample-receiving chamber. The reagent includes a combination of components, and is formulated to dry rapidly with minimal or no running after deposition.

This stripe may be applied in any suitable fashion which provides the desired extent and uniformity of thickness, precision of the stripe edge, homogeneity, and the like. Preferred methods are capable of applying the desired coating at relatively high speed and high batch size. Suitable methods of application are well known in the art and therefore are not detailed herein.

Preparing the Spacing Layer

Referring now to process line 114, a process flow for preparing the spacing layer is illustrated. Beginning at stage 116, a material is selected to prepare a spacing layer for laminating on top of the reagent coated web prepared at stage 112. The base film for the substrate can be selected from a variety of materials. The spacing layer material, similar to the base layer, can be provided as an elongate roll which can be conveniently processed rapidly and with high efficiency. Preferred materials include a polyester film sold under the trade name MELINEX® by DuPont. Other materials suitable for use in the present invention could include PEN. The spacing layer material has a thickness specifically selected to provide a desired chamber depth (or height) in each of the test strips when combined with the thicknesses of any joining layers that are used to laminate the spacer to the other strip components. In preferred embodiments, the spacing layer is selected to have a thickness between about 75 µm and about 150 µm, more preferably from about 100 µm to about 125 µm. As noted above, the spacing layer can be formed of a double-sided adhesive.

The spacing layer is preferably formed as a continuous film having a series of gaps that will align with the electrodes on the bottom substrate webbing. The manner of joining the spacing layer and bottom substrate will impact the method for preparing the spacing layer. For example, if the spacing layer is to be heat welded to the bottom substrate, then the spacing layer may simply be die cut to provide the appropriately spaced chamber gaps. However, a preferred method is the use of thin, non-interfering adhesives that join the adjacent layers. In accordance with this preferred method, a spacing layer is prepared for combination with the previously described substrate webbing as set forth hereafter.

The spacing layer film is prepared having the desired width for combination with the remainder of the test strip components. The spacing layer film may include an opaque portion, e.g., a section 23 of it is printed blue or another color for use in visualizing the sample-receiving chamber, as described elsewhere. The spacing layer film is laminated on the bottom side with a combination adhesive and release liner, and on the top side with a similar combination adhesive and liner.

At stage 118, two transfer adhesives are laminated to the spacing layer material: the first transfer adhesive is laminated to the top surface of the spacing layer, and the second transfer adhesive is laminated to the bottom surface of the spacing layer. Preferably, the transfer adhesives are the same adhesive; however, in alternative embodiments, the first and second transfer adhesives can be different from each other. In preferred embodiments, the transfer adhesives are selected from commonly used and known adhesives, including pressure sensitive adhesives. Preferred adhesives exhibit sufficient hydrophobicity to prevent or inhibit the test sample in the chamber from wicking out between the spacing layer and the reagent layer or base substrate. An example of a suitable sensitive adhesive is ARCare 90132 from Adhesives Research Inc. The adhesives are provided with a release liner to prevent premature adhesion of the spacing layer during processing. The release liners are disposed on the exterior surface of the first and second transfer adhesives, facing outward from the spacing layer material.

The spacing layer with the adhesive release liners on the top and bottom surfaces progresses to stage 120. At stage 120, the cavity which will form the sample-receiving chamber is punched in the spacing layer. In one embodiment, the cavity is punched using a "kiss cut" method. The kiss cut method cuts through the upper release liner, the upper adhesive, the spacing layer, and the lower adhesive, but not through the lower release liner. In subsequent operations, simply removing the lower release liner will then remove the punched out portions of the lower adhesive, the spacing layer, the upper adhesive, and the upper release liner from the punched spacing layer. In other embodiments, the cavity can be punched through with a hollow die. The hollow die completely punches or cuts through the spacing layer, the two adhesives, and the two release liners, with the punched out portion subsequently removed in the hollow die. The spacing or pitch between each cavity is determined and accurately controlled to allow accurate mating of the punched spacing layer over the electrodes using one or both of the indexing marks patterned in the reagent-coated web.

At stage 122, the lower release liner on the spacing layer is removed, taking with it the kiss cut portions and exposing the adhesive on the underside surface of the spacing layer. Proceeding on to stage 124 in process line 101, the spacing layer is laminated over the reagent-coated web using one or more of the indexing marks previously patterned on the web to correctly align each cavity formed in the punched spacing layer directly on top of an electrode set to provide a web-spacing layer laminate. At stage 126 in the central process line 101, the upper release liner covering the upper adhesive on the web-spacing layer laminate is removed in preparation for attaching the cover layer.

Laminating on the Cover Portions

At stage 128, a material for a body cover is introduced into the process. In preferred examples, the material is a flexible polymeric material and may be selected, for example, MELINEX 454 or MELINEX 339 from du Pont. The material for the body cover is sized to have a width sufficient to overlay at least a portion of the electrode traces in the sample-receiving chamber of the test strip.

Referring now to process line 130, beginning at stage 131, a film material is selected to provide a chamber cover over the cavity, reagent, and measuring electrodes on the web-spacing layer laminate. In preferred embodiments, the chamber cover material is provided as a clear poly(ethylene-terephthalate) (PET) or poly(ethylene-naphthalate) (PEN) film having a thickness between about 100 µm and about 200 µm. The coating may preferably include a release liner, which can be removed immediately prior to laminating over the web-spacing layer. The chamber cover is preferably made from a hydrophilic material or the bottom surface of the chamber cover may be treated or coated to make it hydrophilic as indicated at 134.

At stage 138, the film material can be sized to a desired width sufficient to form the chamber cover to overlay the cavity and electrodes.

Proceeding to stage 140, the body cover from stage 128 and the chamber cover from stage 138 are laminated to the web-spacing layer laminate. In preferred embodiments, the body cover and chamber cover are simultaneously laminated with the web-spacing layer laminate. The body cover is positioned over a portion of the electrode traces proximate to the electrodes formed on the base substrate. The chamber cover is positioned over the cavity, reagent, and measuring electrodes on the web-spacing layer laminate. The body cover and chamber cover are separated by a gap to form a vent at the interior end of the cavity formed in the test strip.

As described, the chamber cover is placed near the edge of the strip to overlie the cut out portion of the spacing layer, leaving the innermost portion of the cut out uncovered. As just described, this chamber cover preferably includes a hydrophilic underside to promote the wicking of fluid into the reagent chamber. The chamber cover is spaced slightly from the body cover to form a gap which thereby communicates with the sample-receiving chamber and serves as a vent opening for air to escape as fluid enters the chamber, as described above.

The opacity of the spacing layer and the transparency of the chamber cover cooperate to allow a user of the final test strip to better view the progress of a test. As constructed, the bottom substrate or reagent layer coated thereon is visible through the cut out in the spacing layer and through the transparent chamber cover. The bottom substrate and/or reagent has a light color, e.g., bright yellow, which contrasts with the opaque coloring of the spacing layer. Therefore, the progress of a fluid through the capillary channel can be easily monitored by the person using the test. Further, since the slot 34 is configured to be hydrophobic on the body cover side and hydrophilic on the chamber cover side, fluid will abruptly stop when it reaches the slot, thus presenting a sharply defined fill-line which in turn provides a clear indication to the user that sufficient fluid sample has been received into the chamber.

Separating the Test Strips

From stage 140, the finish processing steps for the fabrication of test strips are performed. At stage 142, a decision is made whether to manufacture a single, die-cut test strip similar to the single test strip 10 above discussed. If so, then the multi-layered laminate from stage 142 proceeds to stage 144 to be die cut into single test strips.

Alternatively, the multi-layered laminate from stage 142 proceeds to stage 148, where it is kiss cut to define individual test strips and to perforate or weaken the boundaries between adjacent test strips on the ribbon. Additionally, at stage 149 the ends of the test strips are die cut along the laminated ribbon. One end of the web is cut to form the fluid receiving end of the test sensor with a Y-shaped opening leading into the cavity. The test strips may be divided into cards comprising a number, e.g., 25, of strips which are only fence cut and then folded to be stacked in a vial or dispenser.

Proceeding out of either stage 144 or 149, the processed strips or ribbon of strips are inspected and ultimately packaged for use by the consumer at stage 146 or 150, respectively.

Figure 6:
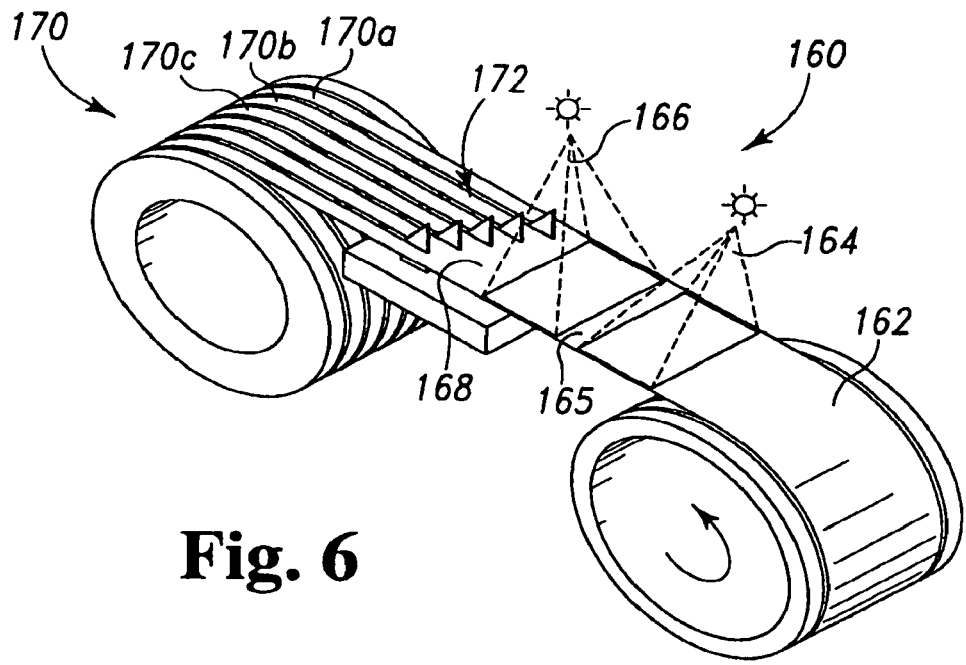
FIG. 6 is a perspective view showing the reel-to-reel processing and cutting of a web material useful in forming the bottom substrate of the biosensor of the present invention.

FIGS. 6-16 illustrate in greater detail some of the components and/or process stages previously described with respect to FIGS. 5 and 5A. FIG. 6 illustrates a perspective view of one embodiment of a base film for use in forming the test strip. Base film 160 is preferably provided as a flexible film or web material that is rolled onto one or more rollers 162 with processes 164, 166 proceeding on the material between the rollers.

The pretreated upper surface of the film is metallized using a sputtering, PVD, CVD, EBPVD, MOCVD or another suitable process, illustrated by reference number 166 and described more fully above, to deposit a uniform coating of a metal or metal alloy. The processes can use a single or multiple target source for the metallic layer. The metallized film 168 can then be sectioned or subdivided into a plurality of metallized films, e.g., 170a, 170b, and 170c, by cutting or slicing the film as illustrated by reference number 172. Each separated roll of the conductive, metallized film 170 can then be rolled upon a single core or upon a plurality of different cores as preferably desired.

Figure 7:
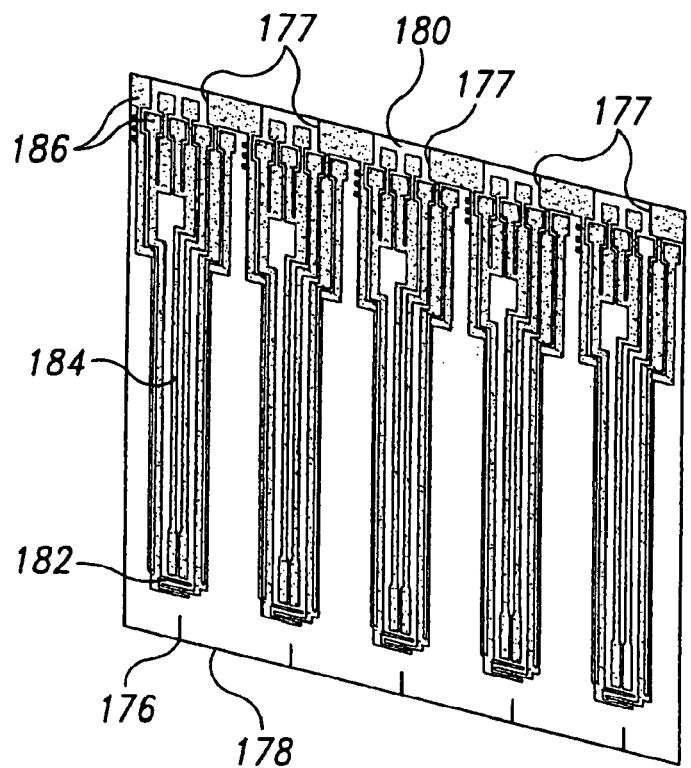
FIG. 7 is a perspective view of a portion of a webbing, showing an exemplary pattern of electrical components on the base substrate.

The electrical components are formed from the conductive film, as shown in one embodiment in FIG. 7. The metallic surface of film 170 is treated to remove any metallic component that is not desired to form the electrodes, traces, contact pads, or other intended features. This process can be precisely controlled using laser ablation or other technology. The process provides a plurality of sets of electrodes 182, traces 184, and contact pads 186. The process can also provide a plurality of indexing or registration marks 176 along a first edge 178 and/or similar registration marks 177 along the opposite edge 180. As shown in FIG. 7, repeating features of the electrode pattern form registration markings 177. Preferably, each set of electrodes and/or contacts is associated with at least one index or registration mark, 176 and 177, respectively.

Figure 8:
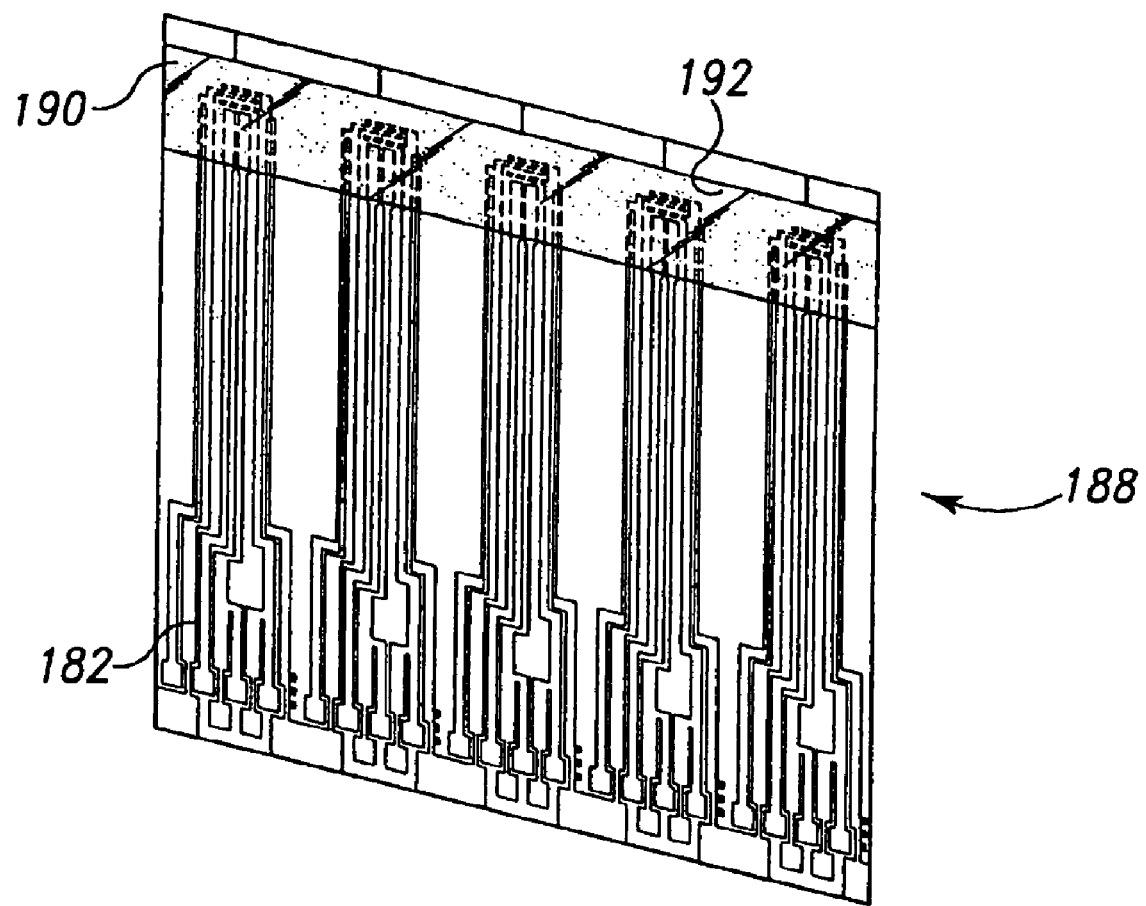
FIG. 8 is a perspective view of a portion of the webbing of FIG. 7 and including a reagent composition coated thereon.

FIG. 8 illustrates a portion of a reagent-coated web 188. The reagent composition is deposited on the surface of the flexible web material. The reagent layer 190 is deposited using a variety of coating methods including curtain coating, hot melt coating, rotary screen coating, doctor blade or air knife coating, Meyer bar coating, and reverse roll coating techniques. Preferably, the reagent layer is deposited on the flexible web as a wet composition at a thickness of between about 50 µm and about 100 µm, more preferably, between about 60 µm and about 80 µm. Web 188 can be provided by coating a uniformly thin layer of reagent 190 directly on top of electrode sets 182 and along the length of web 188 as a continuous narrow band 192. In preferred embodiments, the narrow band 192 has a width of between about 5 mm and 9 mm and a dry thickness of between about 2 µm and about 10 µm. As depicted in FIG. 8, the reagent layer 190 is translucent.

Figure 9:
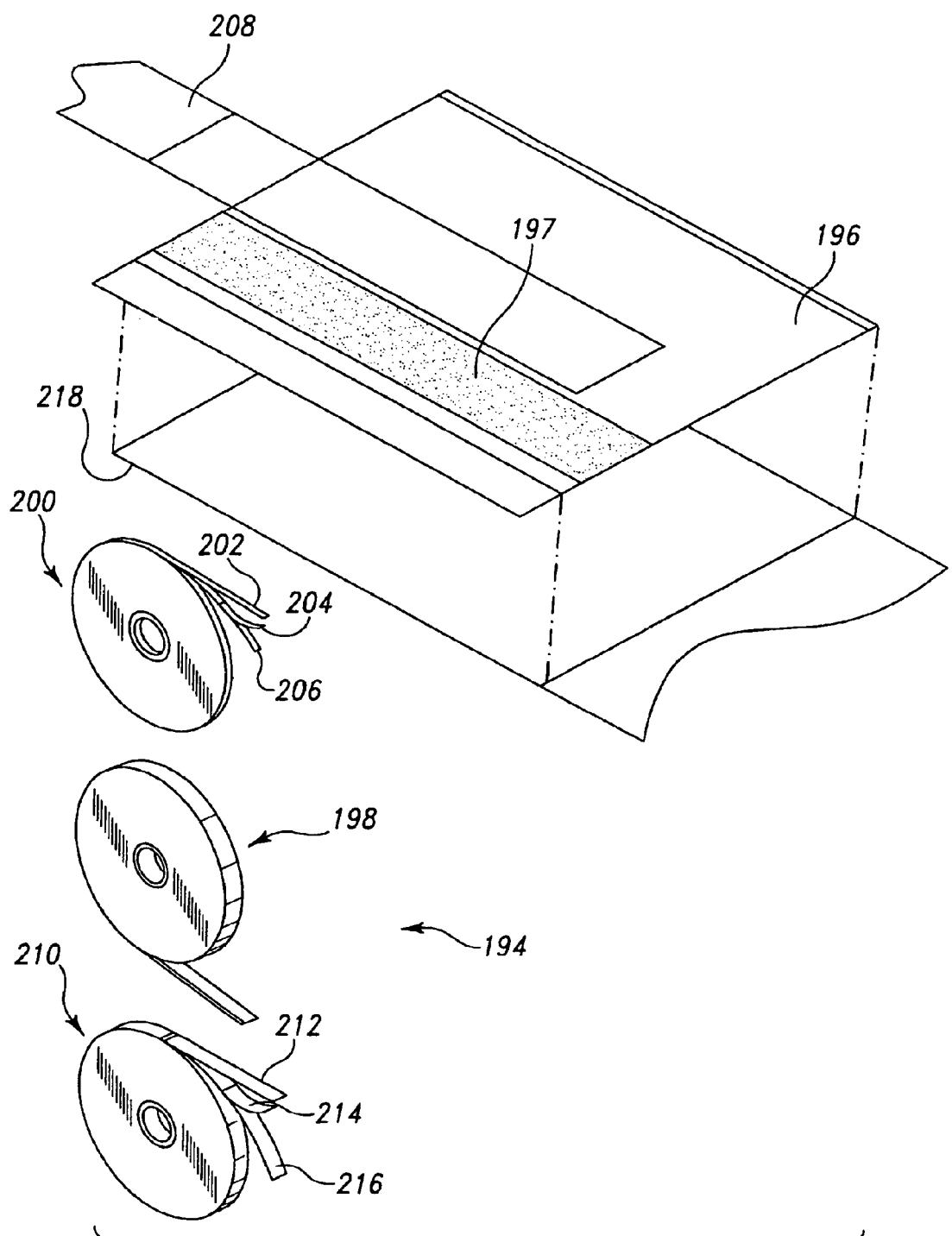
FIG. 9 is an exploded, perspective view showing a spacing layer and the associated adhesive layers and release liners.

FIG. 9 is an exploded view of a spacing layer assembly 194, which can be assembled in accordance with the present invention. Spacing layer assembly 194 comprises a spacing layer 196 preferably formed of a polymeric material. Spacing layer 196 includes a band or section 197 that is colored (corresponding to section 23, FIG. 2). In the manufacturing process, spacing layer 196 is provided in a roll 198 and is then over-coated with adhesives on top and bottom.

The top adhesive is provided in a roll 200 which further comprises a top or "tight" release liner 202, which is adapted to withstand further processing, an adhesive 204, and a lower or "easy" release liner 206. Preferred adhesives 204 for use in the present invention include a pressure-sensitive adhesive sold under the trade name ARCare 90132 by Adhesives Research Inc. During assembly, bottom release liner 206 is removed and the resulting adhesive 208 having the top release liner 202 still present is adhered to spacing layer 196 as indicated in the top of FIG. 9.

Similarly, the bottom adhesive is provided in a roll 210 which further comprises a top or "tight" release liner 212, which is adapted to withstand further processing, an adhesive 214, and a lower or "easy" release liner 216. Preferred adhesives 214 for use in the present invention include a pressure-sensitive adhesive sold under the trade name ARCare 90132 by Adhesives Research Inc. During assembly, bottom release liner 216 is removed and the resulting adhesive 218 having its top release liner 212 facing away from spacing layer 196 is adhered to spacing layer 196 as indicated in FIG. 9. It should be understood that adhesive 204 can be the same or different from adhesive 214.

Figure 10:
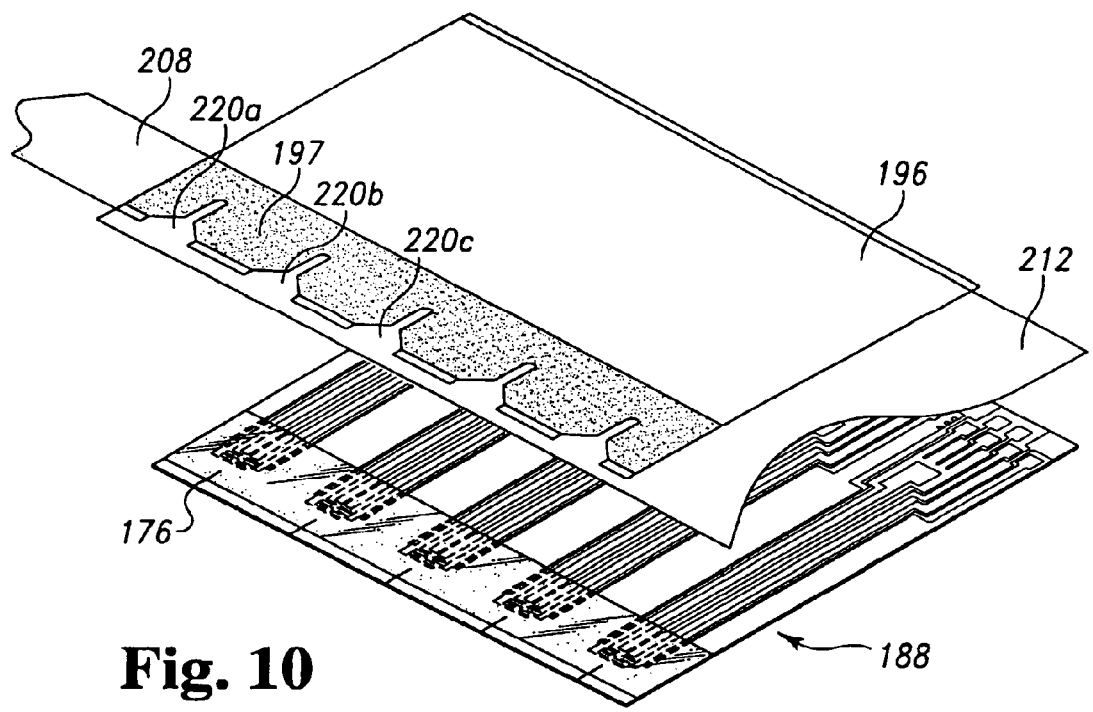
FIG. 10 is an exploded perspective view of a portion of the spacing layer with pre-capillary chambers cut out and the spacing layer being aligned for lamination to a base substrate having electrode patterns thereon.

FIG. 10 illustrates spacing layer 196 that has been die cut to form pre-capillaries 220a, 220b, 220c, etc., and is ready to be laminated to a web of base substrate material 188 as described with reference to FIG. 8. Pre-capillaries 220 can be formed using a "kiss-cut" technique in which a die cuts through the top release liner 202, adhesive 204, spacing layer 196, and adhesive 214, but not release liner 212, which, as noted above, faces away from spacing layer 196. Release liner 212 is then removed along with portions of the top release liner 202, adhesive 204, spacing layer 196, and adhesive 214 that had been cut through. These portions that are cut through comprise "capillary trim," i.e., a sandwich of layers shaped like pre-capillaries 220. This "trim" is removed along with release liner 212, leaving the cavities 220 devoid of any material. As release liner 212 is removed, it can be inspected to ensure that it always contains the capillary trim just described. The resulting series of cavities 220 are spaced from each other a desired distance selected to position each one of the channels of the series of channels 220 directly over a measuring electrode set in the test strip. The spacing layer 196 having its lower adhesive exposed can then be aligned with web 188 by means of indexing marks 176 and laminated thereto. Each capillary channel of the series of channels 220 overlays one set of measuring electrodes 182.

Figure 11:
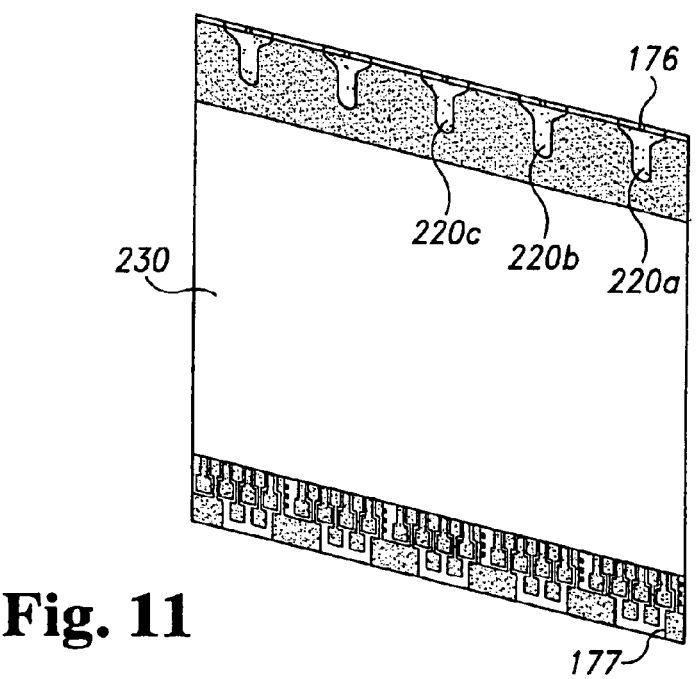
FIG. 11 is a perspective view of an assembly of the base substrate with the spacing layer.
Figure 12:
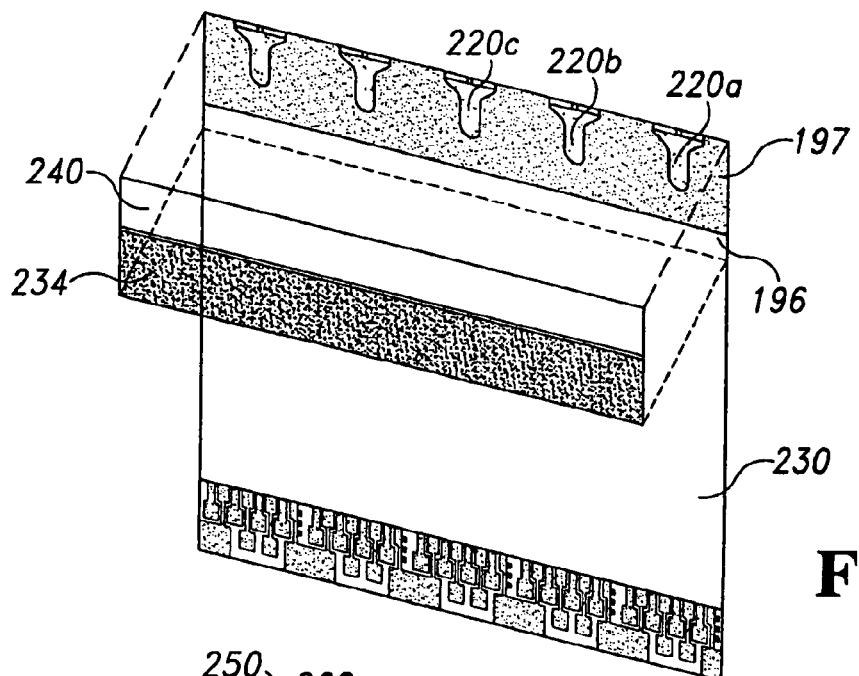
FIG. 12 is an exploded, perspective view showing the combination of the body and chamber covers for assembly onto the base substrate and spacing layer.

FIG. 11 illustrates an assembly 230 formed by the lamination of spacing layer 196 to web 188. In FIG. 11, the upper release liner 202 has been removed from the top adhesive 208, which makes assembly 230 ready for assembly of additional material thereto. As shown in FIG. 12, a web 240 of chamber covering layer material and a web 234 of body covering material are aligned over the exposed upper adhesive 208 of assembly 230 and are ready to be adhered thereto. As depicted in FIG. 12, chamber covering layer 240 is clear and includes a hydrophilic coating (see coating 21, FIG. 2) on at least the side that faces cavities 220. This facilitates wicking or transport of the liquid sample into the sample-receiving chamber and over the electrodes and reagent layer. Body cover 234 is opaque, is colored as shown, and is preferably hydrophobic. Covering layer 240 and body cover 234 can be provided on reels like those described above with reference to FIG. 9.

Preferably, chamber covering material 240 is slightly thinner than body covering material 234. After the chamber covering material 240 and body covering material 234 are laminated to the other layers (described below), the assembly is rewound to await the final processing steps. If body covering material 234 is thicker than chamber covering material 240, then body covering material 234 will absorb more of the pressure or force imparted to the web as it is rewound and stored. Thus, if any adhesive squeezes out of the web as it is rewound, the adhesive will squeeze out around the body covering material 234 and not the chamber covering material 240. Advantageously, the thinner chamber cover thus reduces the possibility of the adhesive squeezing out from under it during roll processing and entering the capillary zone where it could degrade or destroy the test strips ultimately produced.

Figure 13:
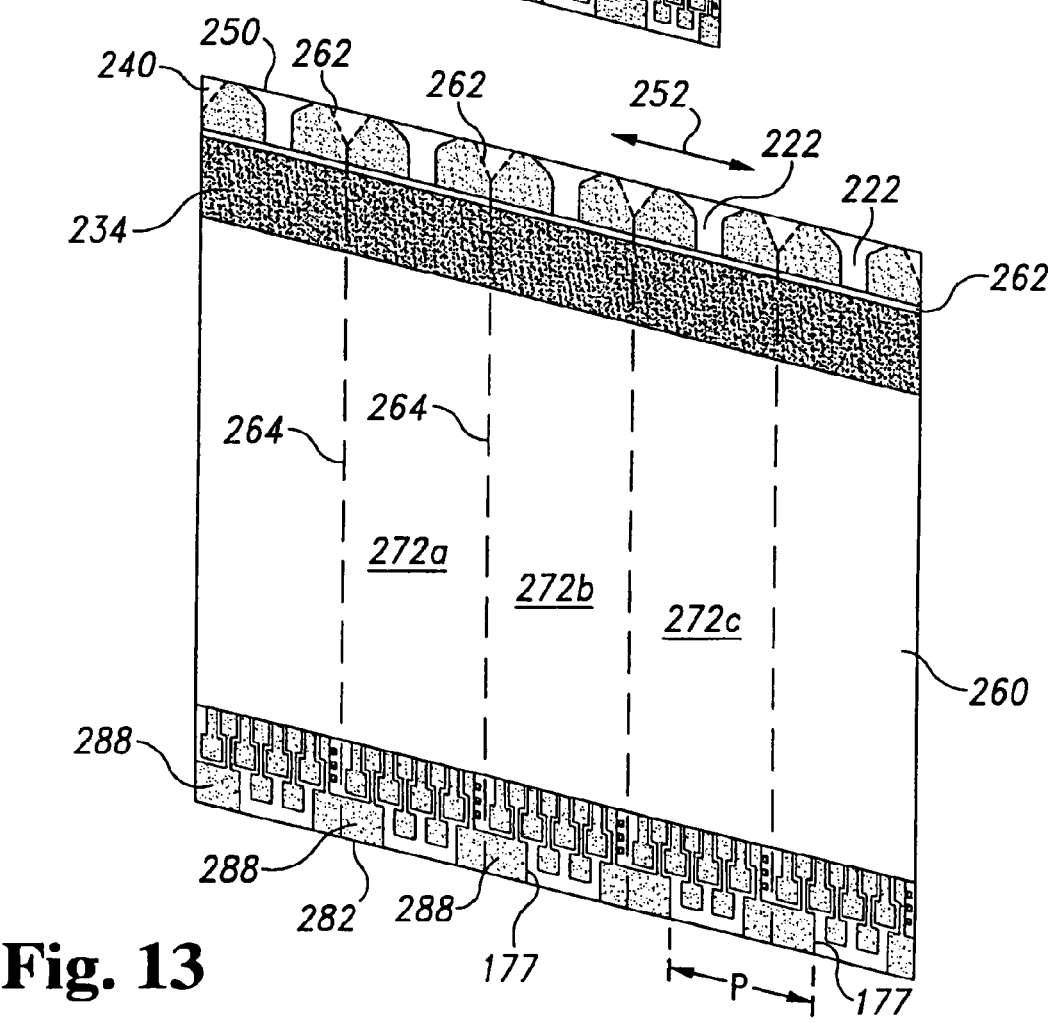
FIG. 13 is a perspective view of a portion of an assembly including the several layers comprising the biosensor.

Assembly 260 shown in FIG. 13 is produced by laminating webs 234 and 240 to the assembly 230 shown in FIG. 12 and then trimming the end of the web to form dosing edge 250. Dosing edge 250 is preferably formed by a shear cut in which the cutting blade moves across the end of the web as indicated by arrow 252. By contrast, it is more difficult to use a die punching technique without damaging the capillaries. The shear cut along dosing edge 250 also cuts away a portion of the pre-capillaries 220 and defines the final volume of capillaries 222. Capillaries 222 preferably include a flared or Y-shaped opening as shown. Preferably, a gap 262 is formed between the chamber covering web and the body covering web and this gap will ultimately provide a vent opening in the individual test strips. In preferred embodiments, the gap has a width of between 1.0 mm and about 1.6 mm. As noted above, however, the gap could be replaced by using a unitary covering layer having a notch formed on its underside (FIG. 1B) or by having the chamber cover overlap the body cover or vice versa. (FIG. 1C).

Figure 14:
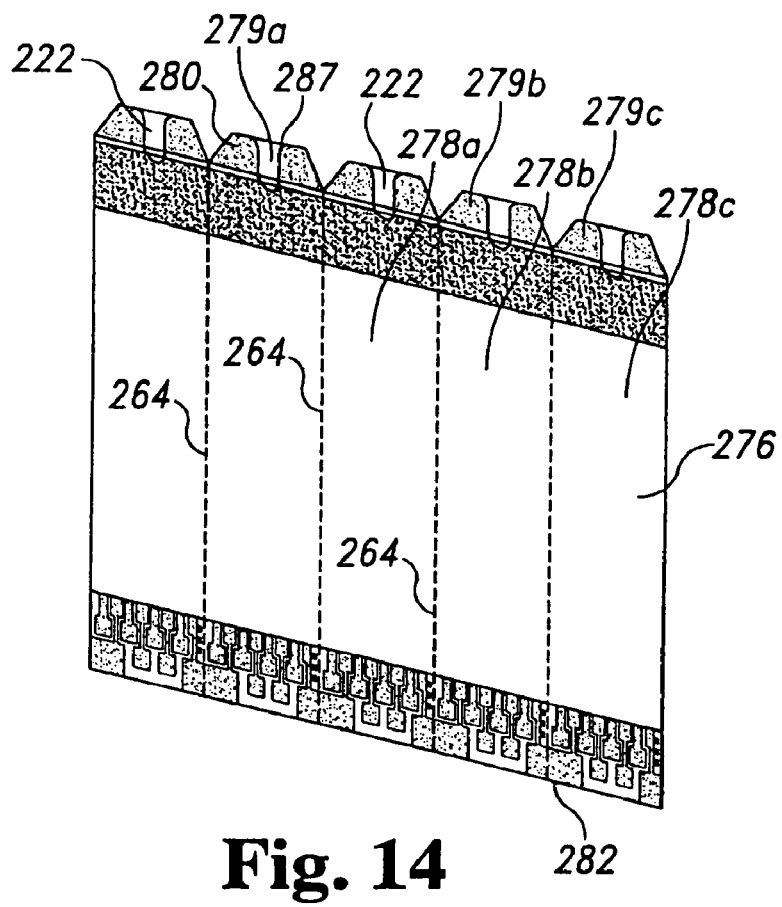
FIG. 14 is a perspective view of a portion of webbing including several detachable biosensors.

With further reference to FIG. 13, assembly 260 is ready for further processing as indicated by dashed lines 262 and 264. In FIG. 14 there is shown the kiss-cut strip 276 having a plurality of individual test strips, e.g., 278*a*, 278*b*, and 278*c*, detachably connected together. It can be observed that kiss-cut strip 276 has been trimmed or cut at its upper end along lines 262 in FIG. 13 to have a profile and/or configuration suitable to facilitate capturing a very small fluid sample in each of the series of capillary channels 222. In the illustrated embodiment, kiss-cut strip 276 has a flat working end 280 exposing the end of the sets of Y-cut capillary channels 222. The resulting configuration of second edge 282 can be provided to facilitate insertion of a single strip into a meter (not shown). For example, the second edge 282 can have a registration mark and/or tabs, cut slots, or other configurations designed to allow insertion of a single strip into the meter in only one direction (see arrow 31, FIG. 1)

With reference to FIG. 13, the edges 177 of contact pads 288 are spaced by a constant pitch, "P" as shown, and edges 177 can therefore be used as registration marks. As in other processing steps, the indexing or registration marks 176 and 177 on either the first edge and/or the second edge can be used to accurately "kiss cut" and trim the individual test strips from the laminated structure 260.

Figure 15:
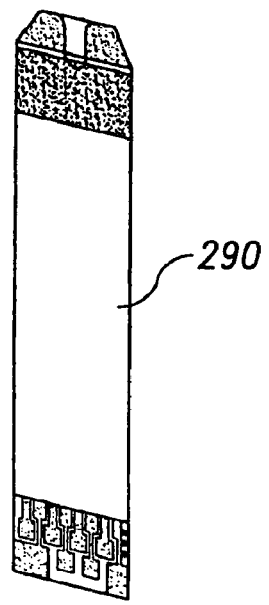
FIG. 15 is a perspective view of a single biosensor separated from the assembled webbing.

FIG. 15 is a perspective view of one embodiment of a punched cut test strip 290 formed by cutting through the dashed lines 264 shown in FIGS. 13 and 14. Strip 290 illustrated in FIG. 15 has been substantially described above as test strip 10. Strip 290 is provided as an individual test strip separate from any other test strip.

EXAMPLE

By way of specific example, a test strip is formed based on the described method and using materials as follows. The bottom substrate is surface coated with a 50 nm layer of gold, and is slit to widths of 43-45 mm Laser ablation (308 nm) is performed using a field size of approximately 40 mm×10 mm. The spacing layer assembly includes a spacing layer film of white Melinex™ 339, and a thickness of 0.1016 or 0.127 mm (4 or 5 mil). The bottom and top adhesives are an Adhesive Research Arcare 90132 adhesive at 0.0254 or 0.0127 mm (1 or ½ mil), sandwiched between release liners having a thickness of 0.0508 mm (2 mil). The capillary channels are formed with a width of 1.500 mm, +/−0.050 mm, and a pitch (spacing) of 9 mm, +/−0.150 mm.

The body cover 18 comprises a strip of Melinex 454, 453 or 339 material, 0.127 mm (5 mil) thick. The chamber cover 20 comprises a polyester or polyethylene naphthate material formed, for example, from Melinex 454 or 453, 0.1016 mm (4 mil) thick. As indicated, the chamber cover may be preferably treated or coated to have a hydrophilic underside adjacent to the capillary channel to promote wicking of the blood specimen into the channel. In a preferred embodiment, a Melinex 453 foil (4 mil) for chamber cover 20 is coated on its underside with a hydrophilic material 21, ARCare 90037 from Adhesives Research Inc. Preferably the chamber cover material is initially formed as a wider material, and is slit to the desired width after preparation.

Test Strip Examples

The following materials will be used in the strip:

| | |
|---|---|
| Base substrate layer 12 | Melinex 329-9 mil or 329 - 10 mil |
| Conductive Layer 26 | Sputtered gold - 50 nm |
| Lower Adhesive Layer 49 | AR ARCare 90132 PSA - 1 to 0.5 mil |
| Spacing layer 14 | Melinex 329 or 339 - 4 to 5 mil |
| Adhesive Layer 46 | AR ARCare 90132 PSA - 1 to 0.5 mil |
| Body Cover 18 | Melinex 339 or 329 or 454 - 5 mil |
| Chamber Cover 20 | Melinex 339 or 329 or 454 - 4 mil |
| Hydrophilic foil 21 | ARCare 90037 |

Storage of Strips

Strips may be packaged in a variety of ways. For example, strips may be packaged into flip-top plastic vials (e.g., 10, 25 or 50 count). All containers include desiccant materials necessary to ensure acceptable shelf-life. Test strips preferably display a minimum shelf life of 18 months when stored between 4°-32° C. in tightly closed containers as provided.

While preferred embodiments incorporating the principles of the present invention have been disclosed hereinabove, the present invention is not limited to the disclosed embodiments. Instead, this application is intended to cover such departures from the present disclosure as come within known or customary practice in the art to which this invention pertains and which fall within the limits of the appended claims.

What is claimed is:

1. A test strip, comprising:
   a base substrate having electrodes formed thereon;
   a reagent layer overlying a portion of the base substrate;
   a spacing layer overlying at least the reagent layer;
   a chamber cover overlying a first portion of the spacing layer;
   a body cover overlying a second portion of the spacing layer, the chamber cover and the body cover having a slot therebetween;
   wherein the spacing layer has a void that defines a sample receiving chamber between the base substrate and the chamber cover, wherein the slot is in communication with the sample receiving chamber, the slot defining a vent opening between the chamber cover and the body cover that allows air to escape as fluid enters the sample receiving chamber; and
   wherein the reagent layer is disposed in the sample receiving chamber and covering at least one of the electrodes and extends under the spacing layer and is sandwiched between the spacing layer and the base substrate.

2. The test strip of claim 1, wherein the slot is substantially aligned with an interior end of the sample receiving chamber.

3. The test strip of claim 1, wherein one surface of the spacing layer is adhered to the base substrate and an opposite surface of the spacing layer is adhered to the chamber cover.

4. The test strip of claim 1, wherein the chamber cover comprises a hydrophilic surface adjacent the sample receiving chamber.

5. The test strip of claim 1, wherein the reagent layer extends across the width of the test strip.

6. The test strip of claim 1, wherein the reagent layer substantially covers the bottom of the sample receiving chamber.

7. The test strip of claim 1, wherein the slot is positioned over the reagent layer.

8. The test strip of claim 1, wherein the sample receiving chamber is bounded on the top side thereof by the chamber cover and the underside of the chamber cover is hydrophilic, whereby wicking of sample fluid into the sample receiving chamber is promoted.

9. The test strip of claim 1, wherein the slot comprises a gap that extends between the body cover and the chamber cover and separates the body cover from the chamber cover, the body cover and the chamber cover having substantially straight edges proximate the gap.

10. The test strip of claim 9, wherein the gap is oriented substantially perpendicular to a longitudinal axis of the test strip.

11. The test strip of claim 1, wherein the sample receiving chamber communicates with a fluid receiving opening disposed at an edge of the test strip.

12. The test strip of claim 1, wherein the body cover includes a hydrophobic portion adjacent the slot.

13. The test strip of claim 1, wherein the body cover is adhered to the spacing layer with a hydrophobic adhesive.

14. The test strip of claim 1, wherein the body cover and chamber cover are formed from the same material.

15. The test strip of claim 14, wherein the body cover is treated with a hydrophobic substance and the chamber cover is treated with a hydrophilic substance.

16. The test strip of claim 1, further comprising electrode traces extending from the electrodes along the base substrate and terminating in contact pads at a meter insertion end of the test strip, the contact pads being exposed for electrical connection thereto.

17. The test strip of claim 1, wherein the chamber cover overlies substantially the entire length of the sample receiving chamber.

18. The test strip of claim 17, wherein the chamber cover has about the same length as the sample receiving chamber.

19. The test strip of claim 17, wherein the chamber cover is transparent or translucent above the sample receiving chamber, whereby fluid entering the sample receiving chamber is visible through the chamber cover.

20. The test strip of claim 18, wherein a top surface of the spacing layer adjacent the void and the bottom of the sample receiving chamber have contrasting colors and are visible through the chamber cover.

21. The test strip of claim 1, wherein the base substrate, spacing layer and chamber cover are adhered to one another by one of heat welding, laser welding, heat sensitive adhesives, pressure sensitive adhesives and combinations thereof.

22. The test strip of claim 1, wherein the electrodes are disposed in the sample receiving chamber.

23. The test strip of claim 1, wherein the body cover and chamber cover are aligned end to end and are disposed in substantially the same horizontal plane.

* * * * *

UNITED STATES PATENT AND TRADEMARK OFFICE
CERTIFICATE OF CORRECTION

| | | |
|---|---|---|
| PATENT NO. | : 8,142,721 B2 | Page 1 of 1 |
| APPLICATION NO. | : 12/888990 | |
| DATED | : March 27, 2012 | |
| INVENTOR(S) | : David W. Burke | |

It is certified that error appears in the above-identified patent and that said Letters Patent is hereby corrected as shown below:

Col. 17, line 42, replace "In a preferred embodiment, the sensor comprises a multi-layered, laminate test strip and a covering layer 16." with --In a preferred embodiment, the sensor comprises a multi-layered, laminate test strip 10. As previously described, the laminate includes a base substrate 12, a spacing layer 14, and a covering layer 16.--

Signed and Sealed this
Fifteenth Day of May, 2012

David J. Kappos
*Director of the United States Patent and Trademark Office*